United States Patent
Terskikh

(10) Patent No.: US 10,716,808 B2
(45) Date of Patent: Jul. 21, 2020

(54) METHODS AND COMPOSITIONS TO MODULATE HAIR GROWTH

(71) Applicant: Sanford Burnham Prebys Medical Discovery Institute, La Jolla, CA (US)

(72) Inventor: Alexey V. Terskikh, Solana Beach, CA (US)

(73) Assignee: SANFORD BURNHAM PREBYS MEDICAL DISCOVERY INSTITUTE, La Jolla, CA (US)

( * ) Notice: Subject to any disclaimer, the term of this patent is extended or adjusted under 35 U.S.C. 154(b) by 409 days.

(21) Appl. No.: 15/320,529

(22) PCT Filed: Jul. 7, 2015

(86) PCT No.: PCT/US2015/039397
§ 371 (c)(1),
(2) Date: Dec. 20, 2016

(87) PCT Pub. No.: WO2016/007522
PCT Pub. Date: Jan. 14, 2016

(65) Prior Publication Data
US 2017/0182095 A1 Jun. 29, 2017

Related U.S. Application Data

(60) Provisional application No. 62/022,639, filed on Jul. 9, 2014.

(51) Int. Cl.
*A61K 35/12* (2015.01)
*C12N 5/071* (2010.01)
*C12N 5/0775* (2010.01)
*G01N 33/50* (2006.01)

(52) U.S. Cl.
CPC ............ *A61K 35/12* (2013.01); *C12N 5/0627* (2013.01); *C12N 5/0662* (2013.01); *G01N 33/5044* (2013.01); *C12N 2500/38* (2013.01); *C12N 2501/11* (2013.01); *C12N 2501/115* (2013.01); *C12N 2506/02* (2013.01); *C12N 2506/13* (2013.01); *C12N 2533/30* (2013.01); *C12N 2533/52* (2013.01)

(58) Field of Classification Search
None
See application file for complete search history.

(56) References Cited

U.S. PATENT DOCUMENTS

| 2005/0147652 A1 | 7/2005 | Atkins et al. |
| 2009/0198336 A1 | 8/2009 | Qiao et al. |
| 2010/0261276 A1 | 10/2010 | Park et al. |

FOREIGN PATENT DOCUMENTS

| CN | 101755046 A | 6/2010 |
| JP | 2016522682 A | 8/2016 |
| WO | WO-2015162908 A1 | 10/2015 |
| WO | WO-2016007522 A1 | 1/2016 |

OTHER PUBLICATIONS

Bajpai et al. Molecular stages of rapid and uniform neuralization of human embryonic stem cells. Cell Death Differ 16:807-825 (2009).
Bar-Nur et al. Epigenetic memory and preferential lineage-specific differentiation in induced pluripotent stem cells derived from human pancreatic islet Beta cells. Cell Stem Cell 9:17-23 (2011).
Biernaskie et al. SKPs derive from hair follicle precursors and exhibit properties of adult dermal stem cells. Cell Stem Cell 5:610-623 (2009).
Blanpain et al. Epidermal homeostasis: a balancing act of stem cells in the skin. Nat Rev Mol Cell Biol 10:207-217 (2009).
Bock et al. Reference Maps of human ES and iPS cell variation enable high-throughput characterization of pluripotent cell lines. Cell 144:439-452 (2011).
Botchkarev et al. Molecular biology of hair morphogenesis: development and cycling. J Exp Zool B Mol Dev Evol 298:164-180 (2003).
Botchkarev et al. Molecular control of epithelial-mesenchymal interactions during hair follicle cycling. J Investig Dermatol Symp Proc 8:46-55 (2003).
Boulting et al. A functionally characterized test set of human induced pluripotent stem cells. Nat Biotechnol 29:279-286 (2011).
Bronner-Fraser. Neural crest cell formation and migration in the developing embryo. FASEB J 8:699-706 (1994).
Chermnykh et al. Dermal papilla cells induce keratinocyte tubulogenesis in culture. Histochem Cell Biol 133:567-576 (2010).
Cimadamore et al. Human ESC-Derived Neural Crest Model Reveals a Key Role for SOX2 in Sensory Neurogenesis. Cell Stem Cell 8:538-551 (2011).
Curchoe et al. Early acquisition of neural crest competence during hESCs neuralization. PLoS One 5:e13890 (2010).
Danielian et al. Modification of gene activity in mouse embryos in utero by a tamoxifen-inducible form of Cre recombinase. Curr Biol 8:1323-1326 (1998).
Driskell et al. Hair follicle dermal papilla cells at a glance. J Cell Sci 124:1179-1182 (2011).
Driskell et al. Sox2-positive dermal papilla cells specify hair follicle type in mammalian epidermis. Development 136:2815-2823 (2009).
Fernandes et al. A dermal niche for multipotent adult skin-derived precursor cells. Nat Cell Biol 6:1082-1093 (2004).
Gnedeva et al. Derivation of Hair-Inducing Cell from Human Pluripotent Stem Cells. Derivation of Hair-Inducing Cell from Human Pluripotent Stem Cells. PLoS One 10(1):e0116892 (2015).
Greco et al. A two-step mechanism for stem cell activation during hair regeneration. Cell Stem Cell 4:155-169 (2009).

(Continued)

*Primary Examiner* — Blaine Lankford
(74) *Attorney, Agent, or Firm* — Wilson Sonsini Goodrich & Rosati

(57) ABSTRACT

Embodiments of the methods and compositions provided herein relate to inducing hair growth in a subject. Some embodiments include screening for agents to modulate hair growth.

17 Claims, 15 Drawing Sheets

Specification includes a Sequence Listing.

(56) References Cited

OTHER PUBLICATIONS

Hardy. The secret life of the hair follicle. Trends Genet 8:55-61 (1992).
Hoogduijn et al. Comparative characterization of hair follicle dermal stem cells and bone marrow mesenchymal stem cells. Stem Cells Dev 15:49-60 (2006).
Inamatsu et al. Embryonic dermal condensation and adult dermal papilla induce hair follicles in adult glabrous epidermis through different mechanisms. Dev Growth Differ 48:73-86 (2006).
Jahoda et al. Dermal-epidermal interactions. Adult follicle-derived cell populations and hair growth. Dermatol Clin 14: 573-583 (1996).
Jahoda et al. Induction of hair growth by implantation of cultured dermal papilla cells. Nature 311:560-562 (1984).
Jahoda et al. Trans-species hair growth induction by human hair follicle dermal papillae. Exp Dermatol 10:229-237 (2001).
Jandial et al. Cellular alchemy: induced pluripotent stem cells retain epigenetic memory. World Neurosurg 75:5-6 (2011).
Kim et al. Epigenetic memory in induced pluripotent stem cells. Nature 467:285-290 (2010).
Kishimoto et al. Wnt signaling maintains the hair-inducing activity of the dermal papilla. Genes Dev 14:1181-1185 (2000).
Kodaira et al. Purification and identification of a BMP-like factor from bovine serum. Biochem Biophys Res Commun 345:1224-1231 (2006).
Lichti et al. In vivo regulation of murine hair growth: insights from grafting defined cell populations onto nude mice. J Invest Dermatol 101:124S-129S (1993).
Liu et al. Recapitulation of premature ageing with iPSCs from Hutchinson-Gilford progeria syndrome. Nature 472:221-225 (2011).
Metallo et al. Retinoic acid and bone morphogenetic protein signaling synergize to efficiently direct epithelial differentiation of human embryonic stem cells. Stem Cells 26:372-380 (2008).
Millar. Molecular mechanisms regulating hair follicle development. J Invest Dermatol 118:216-225 (2002).
Mishina et al. Bmpr encodes a type I bone morphogenetic protein receptor that is essential for gastrulation during mouse embryogenesis. Genes Dev 9:3027-3037 (1995).
Moad et al. A novel model of urinary tract differentiation, tissue regeneration, and disease: reprogramming human prostate and bladder cells into induced pluripotent stem cells. Eur Urol 64(5):753-761 (2013).
Mould et al. Integrin alpha 4 beta 1-mediated melanoma cell adhesion and migration on vascular cell Integrin alpha 4 beta 1-mediated melanoma cell adhesion and migration on vascular cell adhesion molecule-1 (VCAM-1) and the alternatively spliced IIICS region of fibronectin. J Biol Chem 269:27224-27230 (1994).
Nagoshi et al. Ontogeny and multipotency of neural crest-derived stem cells in mouse bone marrow, dorsal root ganglia, and whisker pad. Cell Stem Cell 2:392-403 (2008).
PCT/US2015/039397 International Search Report and Written Opinion dated Sep. 24, 2015.
Pittenger et al. Multilineage potential of adult human mesenchymal stem cells. Science 284:143-147 (1999).
Rendl et al. BMP signaling in dermal papilla cells is required for their hair follicle-inductive properties. Genes Dev 22:543-557 (2008).
Rendl et al. Molecular dissection of mesenchymal-epithelial interactions in the hair follicle. PLoS Biol 3:e331 (2005).
Schmidt-Ullrich et al. Molecular principles of hair follicle induction and morphogenesis. Bioessays 27:247-261 (2005).
Sieber-Blum et al. The adult hair follicle: cradle for pluripotent neural crest stem cells. Birth Defects Res C Embryo Today 72:162-172 (2004).
Takahashi et al. Induction of pluripotent stem cells from mouse embryonic and adult fibroblast cultures by defined factors. Cell 126(4):663-676 (2006).
Weinberg et al. Reconstitution of hair follicle development in vivo: determination of follicle formation, hair growth, and hair quality by dermal cells. J Invest Dermatol 100:229-236 (1993).
Winnier et al. Bone morphogenetic protein-4 is required for mesoderm formation and patterning in the mouse. Genes Dev 9:2105-2116 (1995).
Wu et al. Hair follicle reformation induced by dermal papilla cells from human scalp skin. Arch Dermatol Res 298:183-190 (2006).
Wu et al. hMSCs possess the potential to differentiate into DP cells in vivo and in vitro. Cell Biol Int Rep 19(2):37-43 (2012).
Yang et al. Review of hair follicle dermal cells. J Dermatol Sci 57:2-11 (2010).
Yoo et al. Application of mesenchymal stem cells derived from bone marrow and umbilical cord in human hair multiplication. J Dermatol Sci 60(2):74-83 (2010).
Yu et al. Dorsomorphin inhibits BMP signals required for embryogenesis and iron metabolism. Nat Chem Biol 4:33-41 (2008).
Zhang et al. Short-term BMP-4 treatment initiates mesoderm induction in human embryonic stem cells. Blood 111:1933-1941 (2008).
Zhou et al. Generation of human induced pluripotent stem cells from urine samples. Nature Protocols 7(12):2080-2089 (2012).
Zhou et al. Generation of induced pluripotent stem cells using recombinant proteins. Cell Stem Cell 4(5):381-384 (2009).
Zouboulis et al. Human skin stem cells and the ageing process. Exp Gerontol 43: 986-997 (2008).
Anonymous. Human ESC-Derived Hair Inducing Cells for Hair Regeneration I Flintbox. Retrieved from the Internet: URL:https://sanfordburnham.flintbox.com/public/project/26244/ (2 pgs) (2014).
Higgins et al. Microenvironmental reprogramming by three-dimensional culture enables dermal papilla cells to induce de novo human hair-follicle growth. PNAS 110(49):19679-19688 (2013).
Yang et al. Generation of folliculogenic human epithelial stem cells from induced pluripotent stem cells. Nat Commun 5:1-11 (2014).
Kishimoto. Isolation of Hair Mesenchymal Cells by High-Speed Cell Sorting and Verification of Their Inductive Ability on Hair Follicle Reconstitution. Cytometry Research 12(1):11-17 (2002) (English Abstract).
Bell et al. Dermal stem cells can differentiate down an endothelial lineage. Stem Cells Dev 21(16):3019-3030 (2012).
Hirobe. Development of Enteric Ganglia in Rat and Human Embryos: An Immunohistochemical Study Assessed by Neurofilament Expression. Journal of the Japanese Society of Pediatric Surgeons 26(6):1126-1144 (1990) (English Abstract).

METHODS AND COMPOSITIONS TO MODULATE HAIR GROWTH

CROSS-REFERENCE TO RELATED APPLICATIONS

This application is a U.S. National Stage Application of U.S. International Application No. PCT/US2015/039397, filed Jul. 7, 2015, which claims the benefit of U.S. Provisional Application No. 62/022,639, filed Jul. 9, 2014, all of which are incorporated herein by reference in their entirety.

REFERENCE TO SEQUENCE LISTING

The present application is being filed along with a Sequence Listing in electronic format. The Sequence Listing is provided as a file entitled BURNHAM036WO_SEQLIST, created Jun. 30, 2015, which is approximately 1.9 Kb in size. The information in the electronic format of the Sequence Listing is incorporated herein by reference in its entirety.

FIELD OF THE INVENTION

Embodiments of the methods and compositions provided herein relate to inducing hair growth in a subject. Some embodiments include screening for agents to modulate hair growth.

BACKGROUND OF THE INVENTION

It has been suggested that in embryogenesis hair follicles are formed by reciprocal interactions between the epidermis and underlying mesoderm [1,2,3,4]. Dermal Papillae (DP) first arise as cell condensates in the dermis in response to epidermal placode formation. As hair follicles progress in development, epidermal cells in placodes proliferate actively and envelope the dermal condensates, now called dermal papillae, separating them from surrounding dermis [5]. Exposed to these new niche conditions, DP cells acquire the expression of BMP-4, its inhibitor noggin, and the surface markers N-CAM and p-75. Additionally, they secrete specific extracellular matrix proteins (e.g. versican (VCAN)) and show high level of alkaline phosphatase activity (AP) [6]. Using double reporter Lef1-RFP/K14-H2BGFP mice, studies have identified detailed genetic signature of prospectively isolated mouse DP cells [7] and identified Wnt, BMP and FGF singling pathway as a requirement for murine DP maintenance and function [8,9,10]. DP cells play a role in hair growth and cycling [6] and determine hair size and hair type [11,12]. It has been long recognized that DP cells are able to induce hair follicle formation not only in embryogenesis but also postnatal. Vibrissae DP cells induced de novo hair formation when transplanted into the footpad of the adult rat, which is normally a non-haired skin area [13]. Human DP cells isolated from scalp skin contribute to hair formation when transplanted into rodents [14,15] and induce keratinocytes morphogenesis in cultures [16].

DP cells have been proposed as a cell-based treatment for hair loss diseases. However, human DP cells are not suitable for this purpose because they cannot be obtained in necessary amounts and rapidly lose their ability to induce hair follicle formation when cultured [7,8,17,18]. Therefore, there is an unmet need to develop functional DP cells capable of inducing a robust hair growth.

SUMMARY OF THE INVENTION

Some embodiments of the methods and compositions provided herein include a method for inducing hair growth in a subject comprising administering a population of induced dermal papillae cells to the subject. Some embodiments also include obtaining the population of induced dermal papillae cells. In some embodiments, the population of induced dermal papillae cells comprises a marker selected from the group consisting of P-75, nestin, veriscan, smooth muscle actin, alkaline phosphatase, and vimentin.

In some embodiments, the population of induced dermal papillae cells is generated from a population of induced neural crest cells. Some embodiments also include selecting for adherent cells. In some embodiments, the population of induced neural crest cells comprises a marker selected from the group consisting of Sox10, Foxd3, integrin alpha 4, cognate receptor for fibronectin, CD47, CD184, CD44, P-75, and nestin. In some embodiments, the population of induced neural crest cells lacks a marker selected from the group consisting of OCT4, SSEA4, veriscan, smooth muscle actin, and alkaline phosphatase.

In some embodiments, the population of induced neural crest cells is generated from a population of stem cells. Some embodiments also include culturing the population of stem cells under conditions to form clusters of the stem cells. Some embodiments also include culturing the clusters in suspension to form spheres. Some embodiments also include plating the spheres on the surface of a substrate, wherein the surface is coated with fibronectin or polyornithine.

In some embodiments, the population of stem cells comprises cells selected from the group consisting of embryonic stem cells, and induced pluripotent stem cells. In some embodiments, the induced pluripotent stem cells are generated from a source selected from the group consisting of fibroblast, renal epithelial cell, and blood cell. In some embodiments, the population of stem cells comprises cells selected from the group consisting of H9 cells, and human induced pluripotent stem cells generated from human BJ fibroblasts.

In some embodiments, the population of induced dermal papillae cells is obtained from a donor subject. In some embodiments, the donor subject and the subject are the same. In some embodiments, the donor subject and the subject are different.

In some embodiments, the administration comprises subcutaneous transplantation. In some embodiments, the administration is to a location of the subject's skin comprising hair at the location in a population of subjects. In some embodiments, the administration is to a location of the subject's skin selected from the group consisting of scalp, face, upper lip, chin, eyebrow, eyelash, arm, leg, back, torso, and abdomen. In some embodiments, the administration is to a location of the subject's skin comprising scar tissue.

In some embodiments, the subject has alopecia.

In some embodiments, the subject is mammalian. In some embodiments, the subject is human.

Some embodiments of the methods and compositions provided herein include a method for screening an agent to modulate hair growth comprising contacting a population of induced dermal papillae cells with a test agent; and measuring an effect on hair growth in the population of induced dermal papillae cells.

In some embodiments, the effect comprises an increase in the rate of hair growth in the population of induced dermal papillae cells compared to a population of induced dermal papillae cells not contacted with the test agent.

In some embodiments, the effect comprises a decrease in the rate of hair growth in the population of induced dermal papillae cells compared to a population of induced dermal papillae cells not contacted with the test agent.

In some embodiments, the effect comprises growth of hair characteristic of a specific location of a subject's skin selected from the group consisting of scalp, face, upper lip, chin, eyebrow, eyelash, arm, leg, back, torso, and abdomen.

In some embodiments, the subject is mammalian. In some embodiments, the subject is human.

In some embodiments, the population of induced dermal papillae cells is contacted with the test agent in vivo. In some embodiments, the population of induced dermal papillae cells is contacted with the test agent in vitro.

In some embodiments, the population of induced dermal papillae cells comprises a marker selected from the group consisting of P-75, nestin, veriscan, smooth muscle actin, alkaline phosphatase, and vimentin.

In some embodiments, the population of induced dermal papillae cells is generated from a population of induced neural crest cells. Some embodiments also include selecting for adherent cells. In some embodiments, the population of induced neural crest cells comprises a marker selected from the group consisting of Sox10, Foxd3, integrin alpha 4, cognate receptor for fibronectin, CD47, CD184, CD44, P-75, and nestin. In some embodiments, the population of induced neural crest cells lacks a marker selected from the group consisting of OCT4, SSEA4, veriscan, smooth muscle actin, and alkaline phosphatase.

In some embodiments, the population of induced neural crest cells is generated from a population of stem cells. Some embodiments also include culturing the population of stem cells under conditions to form clusters of the stem cells. Some embodiments also include culturing the clusters in suspension to form spheres. Some embodiments also include plating the spheres on the surface of a substrate, wherein the surface is coated with fibronectin or polyornithine.

In some embodiments, the population of stem cells comprises cells selected from the group consisting of embryonic stem cells, and induced pluripotent stem cells. In some embodiments, the induced pluripotent stem cells are generated from a source selected from the group consisting of fibroblast, renal epithelial cell, and blood cell. In some embodiments, the population of stem cells comprises cells selected from the group consisting of H9 cells, and human induced pluripotent stem cells generated from human BJ fibroblasts.

Some embodiments of the methods and compositions provided herein include a method for preparing a population of induced dermal papillae cells comprising: generating the population from a population of induced neural crest cells. Some embodiments also include selecting for adherent cells. In some embodiments, the population of induced dermal papillae cells comprises a marker selected from the group consisting of P-75, nestin, veriscan, smooth muscle actin, alkaline phosphatase, and vimentin. In some embodiments, the population of induced neural crest cells comprises a marker selected from the group consisting of Sox10, Foxd3, integrin alpha 4, cognate receptor for fibronectin, CD47, CD184, CD44, P-75, and nestin. In some embodiments, the population of induced neural crest cells lacks a marker selected from the group consisting of OCT4, SSEA4, veriscan, smooth muscle actin, and alkaline phosphatase.

In some embodiments, the population of induced neural crest cells is generated from a population of stem cells. Some embodiments also include culturing the population of stem cells under conditions to form clusters of the stem cells. Some embodiments also include culturing the clusters in suspension to form spheres. Some embodiments also include plating the spheres on the surface of a substrate, wherein the surface is coated with fibronectin or polyornithine.

In some embodiments, the population of stem cells comprises cells selected from the group consisting of embryonic stem cells, and induced pluripotent stem cells. In some embodiments, the induced pluripotent stem cells are generated from a source selected from the group consisting of fibroblast, renal epithelial cell, and blood cell. In some embodiments, the population of stem cells comprises cells selected from the group consisting of H9 cells, and human induced pluripotent stem cells generated from human BJ fibroblasts.

Some embodiments of the methods and compositions provided herein include a population of induced dermal papillae cells prepared by any one of the foregoing methods.

BRIEF DESCRIPTION OF THE DRAWINGS

FIG. 1A is a schematic representation of the differentiation strategy. FIG. 1B is two photomicrographs depicting expression of migratory NC markers Sox 10 and Foxd3, in hESC-NC cultures. Immunofluorescent staining, DAPI in blue. FIG. 1C is a series of three graphs depicting flow cytometry analysis of NC marker integrin alpha-4 (ITGA4) and hESC markers OCT4 and SSEA4 in hESC-NC cultures. FIG. 1D is a series of photomicrographs depicting expression of p-75, Nestin, Versican, SMA and Alkaline Phosphatase (AP) in hESC-NC, hDP (from normal skin) and hESC-DP cultures. Immunofluorescent staining, DAPI in blue. FIG. 1E is a series of graphs depicting Q-PCR analysis of hDP markers p-75, Nexin-1, Versican, SMA and Vimentin in hESC-DP cultures during DP patterning. Day 0=hESC-NC cells. Levels of gene expression, shown as log of fold change over hESC-NC levels, were normalized to 18S. For each gene the dashed line represents levels of gene expression in hDP cell cultures. Scale bars 100 μm.

FIG. 2A is a series of photomicrographs showing stereo images of the whole mounts of keratinocytes transplanted alone or in combination with mouse neonatal Dermal Cells (mDC), hDP, hESC-DP, hESC differentiated in serum for 14 days (hESC-serum), human hESC-derived Neural Crest cells (hESC-NC) and hESC-NC differentiated to DP for 7 days (hESC-DP 7 days). FIG. 2B is a graph depicting quantification hairs induced by keratinocytes transplanted alone or in combination with mDC, hDP or hESC-DP. FIG. 2C is a graph depicting dynamics of hair inductive capability of ESC-DP cells with time of differentiation from hESC-NC (day 0) shown as number of hairs formed per transplantation (trend visualized by the red line) or hESC differentiated in presence of serum (blue diamond) in comparison with keratinocytes alone (visualized by the dashed line). All data are represented as mean±SEM and were analyzed with one-way ANOVA (Kruskal-Wallis test, Dunn's Multiple Comparison post test). *, $P \leq 0.05$; **, $P \leq 0.001$. Scale bars 1 mm.

FIG. 3A shows stereoscopic observation of the whole mount transplants identified GFP-positive hESC-DP cells in positions of DP (arrows heads) and dermal capsule (arrows) in the newly formed hairs; insets show 2× enlargements of the DP regions. FIG. 3B depicts GFP-labeled hIPSC-DPs can be found in DP and dermal capsule of the hairs: whole mount transplants (GFP/bright field) and 8 μm sections (bright field). Inset, fluorescence image of GFP-positive cells in the DP area of hair follicle (2× enlargement of the white square of DP area in the bright field image). FIGS. 3C and 3D depict GFP-positive DPs of newly formed hairs (GFP/bright field, confocal microscopy) are positive for Versican (Versican, confocal microscopy) and Alkaline Phosphatase (AP, bright field), respectively. FIG. 3E shows rarely (~1%) of newly formed hairs) NC-derived GFP-positive cells were detected in the outer root sheath area (arrows) as well as GFP-positive DP (outlined), with confocal image in the GFP panel. FIG. 3F depicts NC-derived GFP-positive cells were found in hair matrix in transplants (confocal microscopy). Inset shows 2× enlargement of GFP-positive cells; GFP in white. Note multiple melanin granules (in black) present throughout GFP-positive cells. Scale bars 250 μm for FIG. 3A; 50 μm for FIGS. 3B-3F.

FIG. 4A shows photomicrographs depicting morphology and transplantation outcomes of hESC-DP cells derived in the absence or in the presence of selective BMP inhibitor dorsomorphin. Scale bars 50 μm for cell cultures and 0.5 mm for cell transplantations. FIG. 4B is a graph depicting Q-PCR analysis of expression of Versican, Corin, Nexin-1, p-75, Vimentin and SMA in hESC-DP cells in the absence or in the presence of selective BMP inhibitor dorsomorphin. All data are presented as mean±SEM and were analyzed with Student's t-test. *, $P \leq 0.05$; **, $P \leq 0.001$.

FIG. 8A is a series of photomicrographs depicting expression of neuroephitelial markers Sox 2, Sox 9 and nestin in hIPSC-NC cultures. Immunofluorescent staining, DAPI in blue. FIG. 8B is a series of photomicrographs depicting expression of DP markers Smooth Muscle Actin (SMA), P-75 and Nestin in human IPSC-DP cell cultures. Immunofluorescent staining, DAPI in blue. FIG. 8C is a graph depicting Q-PCR analysis of expression of Versican, Nexin-1, p-75, Vimentin and SMA. The levels of gene expression normalized to 18S and shown as log fold change over hESC-NC level of expression. Scale bars 100 μm.

DETAILED DESCRIPTION

Figure 1A:
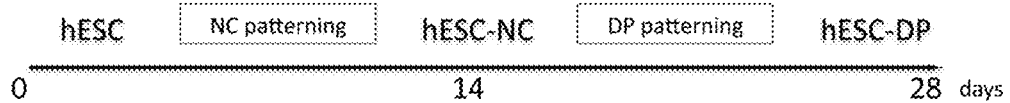
FIGS. 1A-1E depict differentiation of hESCs into DP-like cells via NC intermediate.

Embodiments of the methods and compositions provided herein relate to inducing hair growth in a subject. In some embodiments, a population of induced dermal papillae cells can be generated from a population of induced neural crest cells, which in turn can be generated from a population of stem cells. The population of induced dermal papillae cells can be subcutaneously transplanted into a subject, and generate hair. Advantageously, each population of cells can be amplified to provide a vast population of induced dermal papillae cells available for use, such as use in a transplant.

The induced dermal papillae cells can be used to treat subjects having skin disorders, such as burns, scars, and hair loss. Other embodiments include screening for agents to modulate hair growth. Test agents can contact a population of induced dermal papillae cells and the effects measured. Agents can be tested that produce effects related to rate of hair growth, formation of terminal hair or vellus hair, color of hair shaft, thickness of hair shaft, and level of disulphide bonding in a hair shaft Dermal Papillae (DP) is a unique population of mesenchymal cells that regulate hair follicle formation and growth cycle. During development most DP cells are derived from mesoderm, however, functionally equivalent DP cells of cephalic hairs originate from Neural Crest (NC). NC is a cell population that transiently arises from the dorsal neural tube in development and gives rise to multiple tissues including the peripheral neural system, adrenal medulla, melanocytes and various craniofacial mesenchymal tissues [19]. NC-specific (Wnt1-Cre) lineage tracing using Lox-STOP-Rosa26 or Z/EG reporter mice provided the genetic evidence of NC contribution to a large proportion of cephalic DP cells [20,21,22].

Applicant has developed methods and compositions that include the derivation of functional DP-like cells from human embryonic stem cells (hESCs). See Gnedeva K., et al., "Derivation of Hair-Inducing Cell from Human Pluripotent Stem Cells" (2015) Derivation of Hair-Inducing Cell from Human Pluripotent Stem Cells. PLoS ONE 10(1): e0116892. doi:10.1371/journal.pone.0116892 which is incorporated herein by reference in its entirety. In some embodiments, hESCs may be used to generate NC cells, and then hair-inducing DP-like cells in culture. hESC-derived DP-like cells (hESC-DPs) expressed markers typically found in adult human DP cells (e.g. p-75, nestin, versican, SMA, alkaline phosphatase) and were able to induce hair follicle formation when transplanted under the skin of immunodeficient NUDE mice. hESC-derived DP-like cells engineered to express GFP incorporated into DP of newly formed hair follicles and expressed appropriate markers. BMP signaling is a factor in hESC-DP derivation since BMP inhibitor dorsomorphin eliminated hair-inducing activity from hESC-DP cultures.

Methods for Inducing Hair Growth

Some embodiments of the methods and compositions provided herein include methods for inducing hair growth in a subject. In some such embodiments, a population of induced dermal papillae cells is administered to the subject. Methods of administration can include transplantation of induced dermal papillae cells into the skin of the subject, for example administration can include subcutaneous transplantation of induced dermal papillae cells. The induced dermal papillae cells can be administered to any location of a subject's skin, for example, a location of the subject's skin such scalp, face, upper lip, chin, eyebrow, eyelash, arm, leg, back, torso, hand, foot, and abdomen. In some embodiments, the location of the subject's skin includes scar tissue. In some embodiments, the subject has alopecia. In some embodiments, the subject the subject is mammalian, such as human.

In some embodiments, a population of induced dermal papillae cells can include an isolated population of cells with characteristics of dermal papillae cells that have been generated from other cell types, such as isolated induced neural crest cells. In some embodiments, characteristics of induced dermal papillae cells can include markers associated with dermal papillae cells, such as proteins, expressed nucleic acids, activity to induce hair follicle formation, activity to induce keratinocytes morphogenesis, and activity to induce hair shaft growth. Example markers include BMP-4, noggin, N-CAM, and p-75, extracellular matrix proteins such as versican (VCAN), alkaline phosphatase activity (AP), nestin, smooth muscle actin, and vimentin.

In some embodiments, induced dermal papillae cells can be generated from induced neural crest cells. In some embodiments, adherent cells are selected from a population of induced neural crest cells to generate an isolated population of induced dermal papillae cells. For example, the population of induced neural crest cells can be plated on a substrate, adherent cells can be allowed to attach to the substrate, and non-adherent cells can be washed from the substrate. In some embodiments, the substrate is plastic.

In some embodiments, characteristics of induced neural crest cells can include markers associated with neural crest cells, such as proteins, expressed nucleic acids, activity capable of generating cells such as melanocytes, craniofacial cartilage and bone, smooth muscle, peripheral and enteric neurons and glia. Example markers include Sox10, Foxd3, integrin alpha 4, cognate receptor for fibronectin, CD47, CD184, CD44, P-75, and nestin. In some embodiments the population of induced neural crest cells lack a marker selected from the group consisting of OCT4, SSEA4, veriscan, smooth muscle actin, and alkaline phosphatase.

In some embodiments, induced neural crest cells can be generated from a population of stem cells. Example methods to generate induced neural crest cells from stem cells are described in Bajpai R., et al. Cell Death and Differentiation (2009) 16, 807-825, and Curchoe C L, et al. (2010) Early acquisition of neural crest competence during hESCs neuralization. PLoS One 5: e13890 which are each incorporated by reference in its entirety. In some embodiments, a population of stem cells under conditions to form clusters of the stem cells. In some embodiments, the clusters are cultured in suspension to form spheres. In some embodiments, plating the spheres are plated on the surface of a substrate. In some embodiments, the surface is coated with fibronectin or polyornithine.

In some embodiments, the stem cells include embryonic stem cells, or induced pluripotent stem cells. Induced pluripotent stem cells can be generated from various sources, such as fibroblast, renal epithelial cell, and blood cell. Example methods to generate induced pluripotent stem cells include those described in Takahashi, K. and Yamanaka, S (2006) Cell 126 (4): 663-76; Zhou H, et al. (2009) Cell Stem Cell 4 (5): 381-4; Zhou, et al., (2012) Nature Protocols 7 (12): 2080-2089; and Moad, M., et al. (2013) European Urology 64 (5): 753-761 which are each incorporated by reference in its entirety. In some embodiments, the population of stem cells comprises cells such as H9 cells, or human induced pluripotent stem cells generated from human BJ fibroblasts. In some embodiments, the population of induced dermal papillae cells is obtained from a donor subject. For example, a sample of cells can be taken from a donor subject and a population of induced pluripotent stem cells generated from the sample of cells. In some embodiments, the donor subject and the subject are the same. In some embodiments, the donor subject and the subject are different.

Methods for Screening an Agent to Modulate Hair Growth

Some embodiments of the methods and compositions provided herein include methods for screening an agent to modulate hair growth. Some such embodiments include contacting a population of induced dermal papillae cells with a test agent; and measuring the effect on hair growth in the population of induced dermal papillae cells. In some embodiments, an agent can include a compound, a composition comprising several compounds, and physical conditions such as temperature, and pH.

In some embodiments, the effect can include a change in the rate of hair growth in the population of induced dermal papillae cells compared to a population of induced dermal papillae cells not contacted with the test agent, such as an increase or a decrease in the rate of hair growth in the population of induced dermal papillae cells. The rate of hair growth can be measured by the rate of formation of a hair shaft, or the rate of formation of hair follicles having activity to form a hair shaft.

In some embodiments, the effects can include growth of hair characteristic of a specific location of a subject's skin selected from the group consisting of scalp, face, upper lip, chin, eyebrow, eyelash, arm, leg, back, torso, and abdomen. Example characteristics of hair of a specific location of a subject's skin can include thickness, length, strength of a hair shaft, and length of the hair cycle. In some embodiments, the effects can include growth of hair such as terminal hair, or vellus hair. In some embodiments, the effects can include the color of the hair shaft, such as brown, black, red, white, gray, and blond. In some embodiments, the effects can include the degree of curl in a hair shaft. In some embodiments, the effects can include the thickness of a hair shaft. In some embodiments, the effects can include the level of disulphide bonds in a hair shaft.

In some embodiments, the population of induced dermal papillae cells is contacted with the test agent in vivo. For example, the induced dermal papillae cells may be transplanted into the skin of a subject. In some embodiments, the population of induced dermal papillae cells is contacted with the test agent in vitro.

EXAMPLES

Derivation of hESC-DP Using NC Cells Intermediate

Figure 1B:
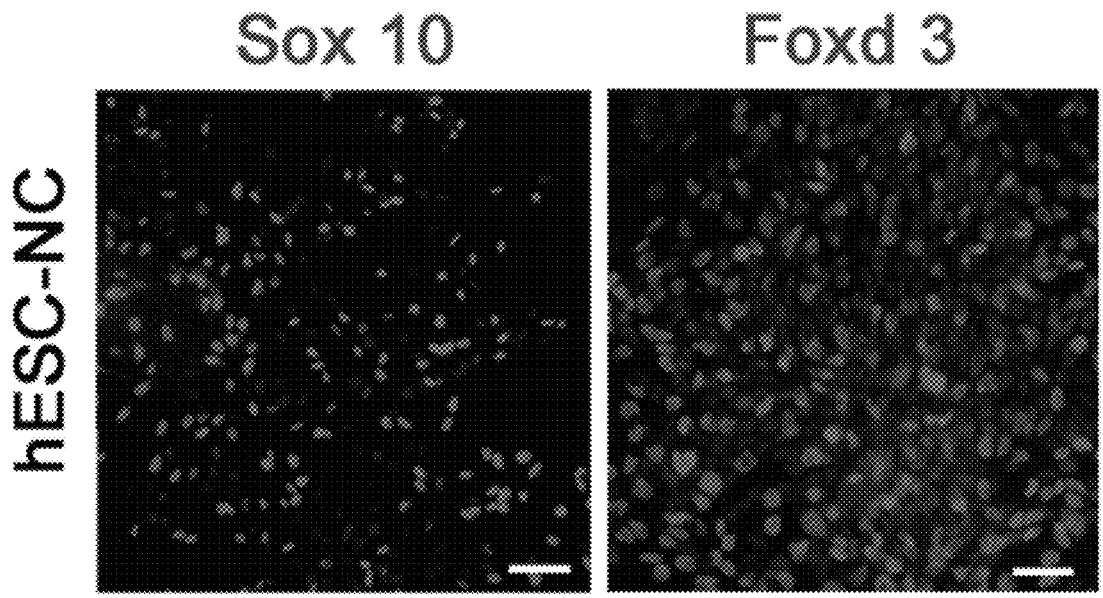
Figure 1C:
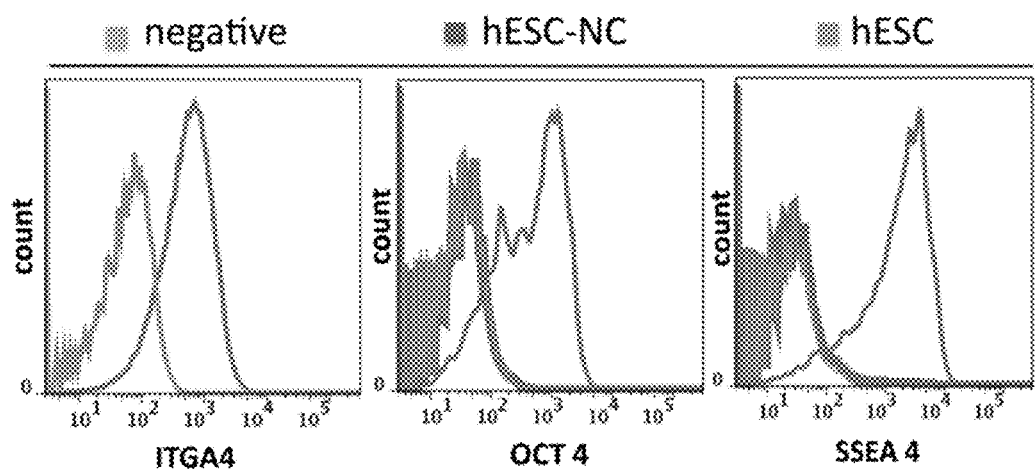

Human DP-like cells were obtained from hESCs via a NC intermediate (FIG. 1A). hESCs were induced to differentiate into hESCs-derived Neural Crest cells (hESC-NC) as previously been described [24,25]. hESC-NC cultures showed robust expression of the neural crest markers Sox10 and Foxd3 (FIG. 1B). Flow cytometry analysis confirmed that nearly 80% of cultured hESC-NC cells express the NC marker Integrin alpha 4 (ITGA4), the cognate receptor for fibronectin [26], and lack the expression of OCT4 and SSEA4 suggesting the absence of undifferentiated hESCs (FIG. 1C).

Figure 5:
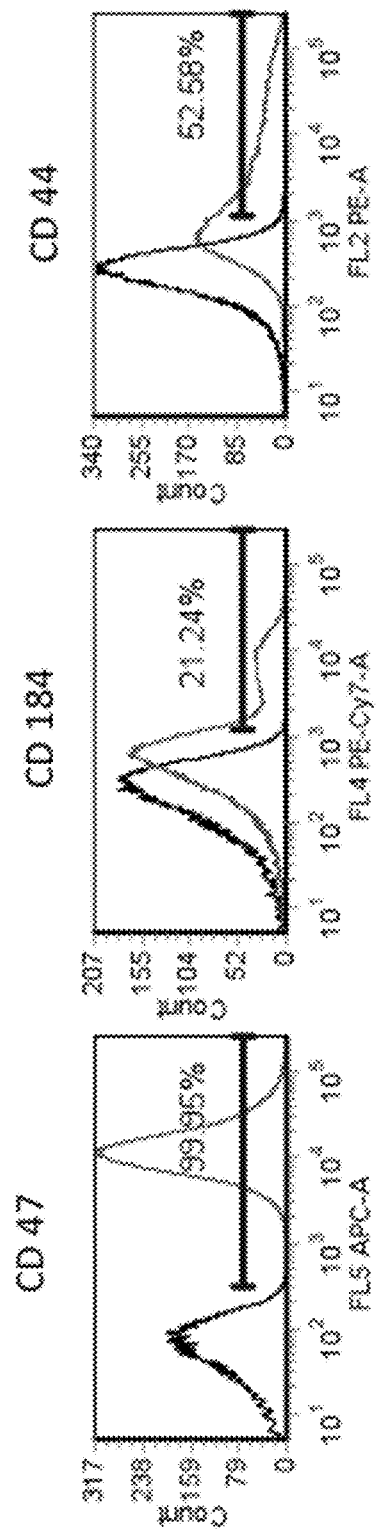
FIG. 5 is a series of graphs depicting expression of mesenchymal markers in hESC-NC with a flow cytometry analysis of mesenchymal markers (CD47, CD184, CD44) expression in hESC-NC cultures.

Neural crest is a multipotent population of cells that give rise to precursors for various mesenchymal tissues [19]. The FACS analysis showed that hESC-NC cells on 14 days of differentiation expressed mesenchymal stem cell markers CD47 (99.95%), CD184 (20%), and CD44 (52.58%) (FIG. 5). To generate DP-like cells, hESC-NCs were further induced to differentiate in DMEM-F12 medium containing 10% FBS for two additional weeks (FIG. 1A). DP cells are somatic dermal stem cells [27] and express mesenchymal stem cell (MSC) markers [28]. Therefore, mesenchymal cells were enriched from differentiating hESC-NCs cultures using preferential adherence to tissue culture plastic [29]. Routinely, about 20% of hESC-NC cultures adhered to plastic and were passaged in serum containing media giving rise to hESC-derived DP-like cells (hESC-DP). These results suggest hESC-derived NC cells contain the mesenchymal progenitor population of cells that can be enriched using an isolation protocol and culture conditions for MSC and DP cells.

Characterization of hESC-DP Cells

Figure 1D:
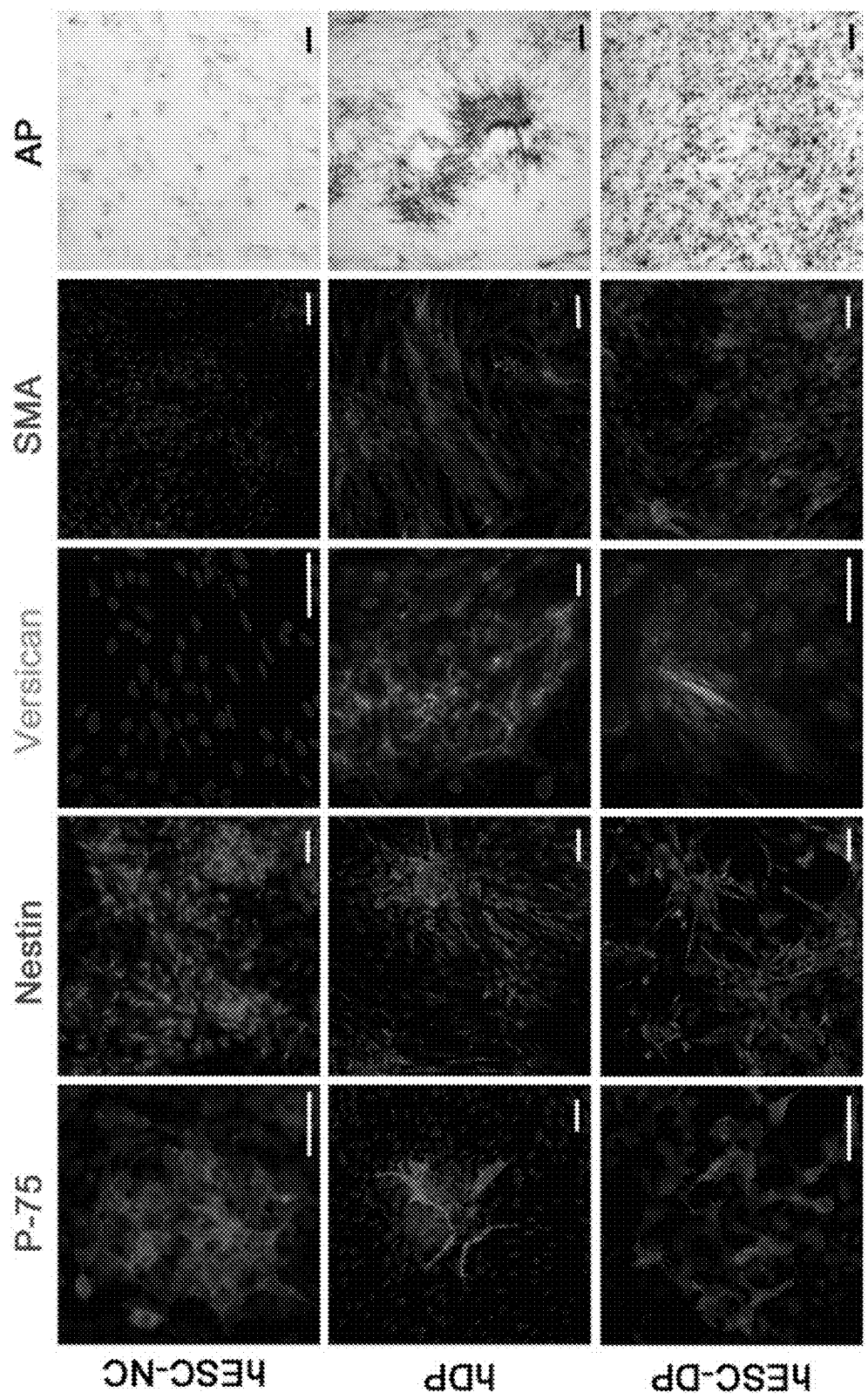
Figure 1E:
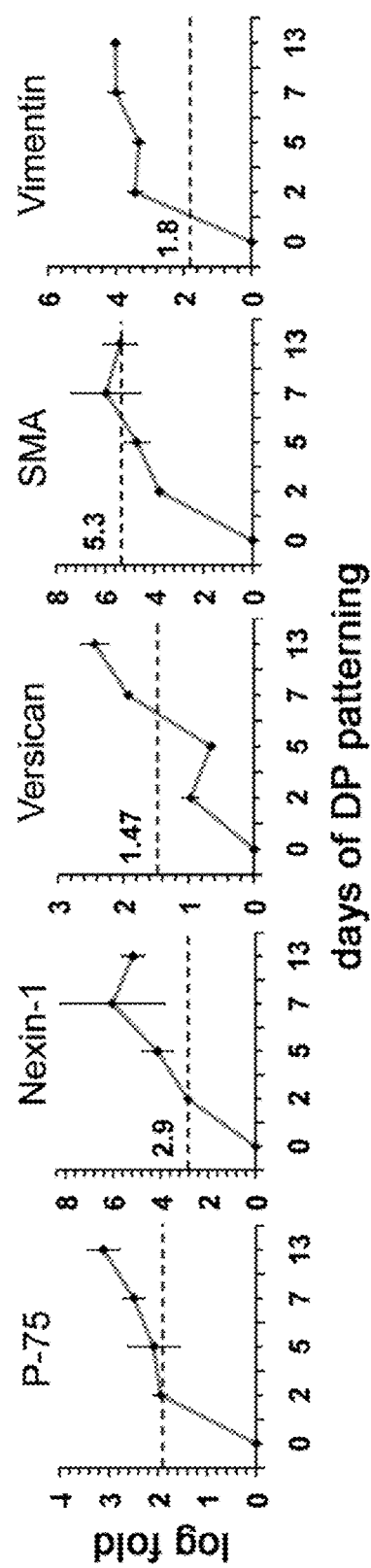
Figure 6:
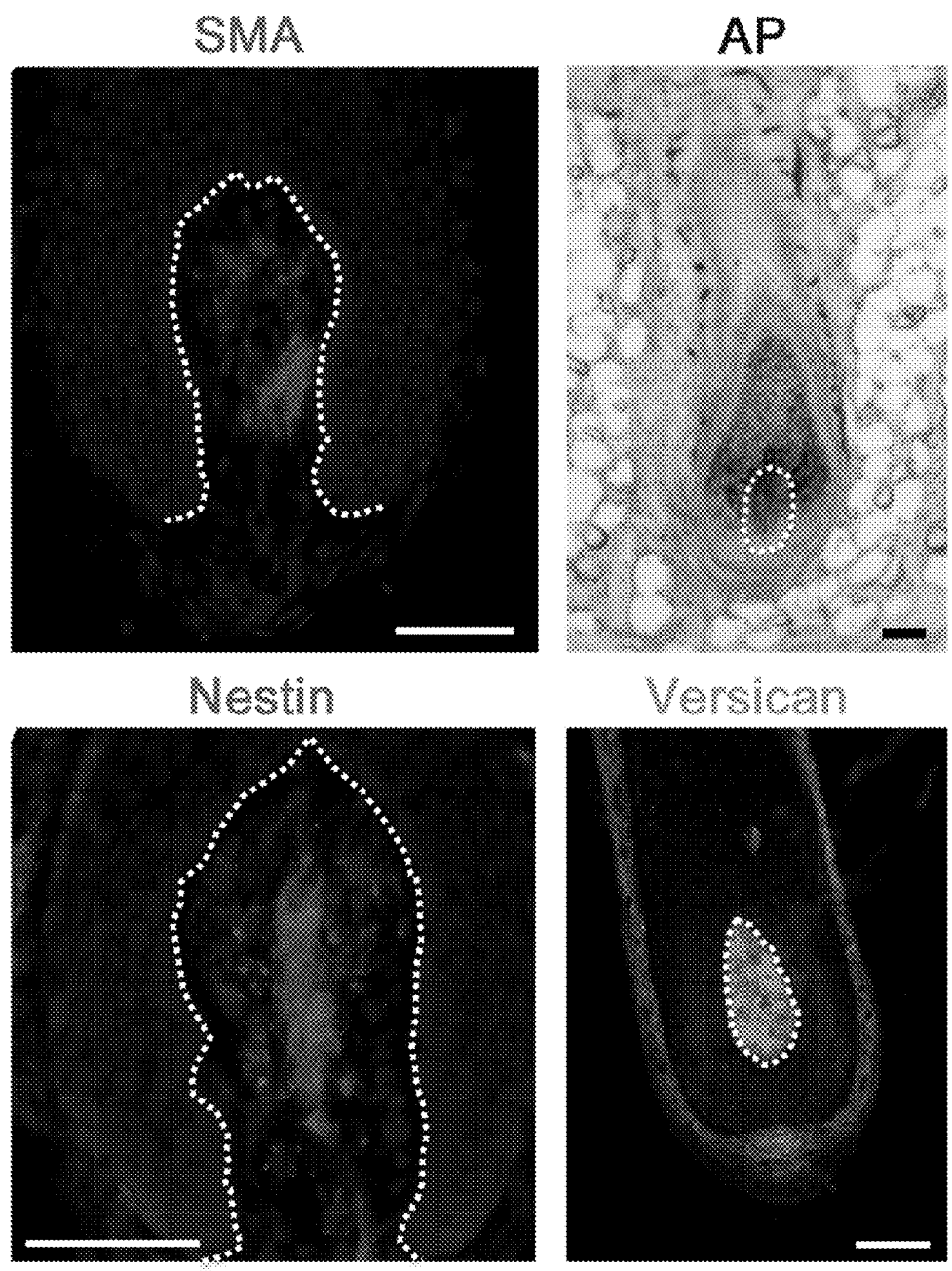
FIG. 6 is a series of photomicrographs depicting expression of DP markers in human hair follicles DP cells in situ. Immunofluorescent staining for SMA, Alkaline Phosphatase (AP), Nestin and Versican Frozen sections; DAPI in blue. Scale bars 100 μm.

The signature genes of mouse dorsal skin DP cells have been compiled [7], however little is known about the gene expression in human cephalic dermal papillae cells. Markers for both mouse and human DP cells were used to characterize mesenchymal hESC-DP. Markers common for DP and neural crest, P-75 and Nestin, were detected in hESC-NC cells, cultured human DP cells (hDP) (isolated from normal human skin) and hESC-DP cells (FIG. 1D) [21]. Other human DP markers: Versican, Smooth Muscle Actin (SMA) and Alkaline Phosphatase (AP) were not detected in hESC-NC cells, but were present in hDP and hESC-DP cultures (FIG. 1D). The specificity of staining for Nestin, Versican, SMA and AP in hDP was confirmed using human scalp skin sections (FIG. 6). The expression of NC markers P-75 (~30%) and Nestin (~90%) in hESC-NC was similar to that in hESC-DP cultures (p-75 ~40%, Nestin ~90%) and showed a close pattern of expression in hDP cells (P-75 ~20%, Nestin ~90%). In contrast, hESC-NC cells were negative for Versican (<1%), SMA (<3%) and completely lacking AP activity, whereas the majority of hESC-DP expressed Versican (~70%), SMA (~70%) and showed high level of AP activity similar to that found in human DP cells, which were nearly 100% positive for Versican, SMA and AP. The overall cell morphology and sub-cellular localization of markers were similar between the cultures of human DP cells and hESC-DPs. To quantitatively evaluate the expression dynamic of DP markers during differentiation of hESC-NC into hESC-DP, Q-PCR analysis was used. The expression levels of all tested human DP markers tested (p-75, Nexin-1, Versican, SMA, and Vimentin) progressively increased during hESC-NC differentiation, and after two weeks were comparable or higher than that found in human-DP cell cultures (FIG. 1E). Taken together, these results suggest the presence of human DP-like cells within hESC-DP cultures.

Hair-Inducing Properties of hESC-DP Upon Transplantation

Figure 2A:
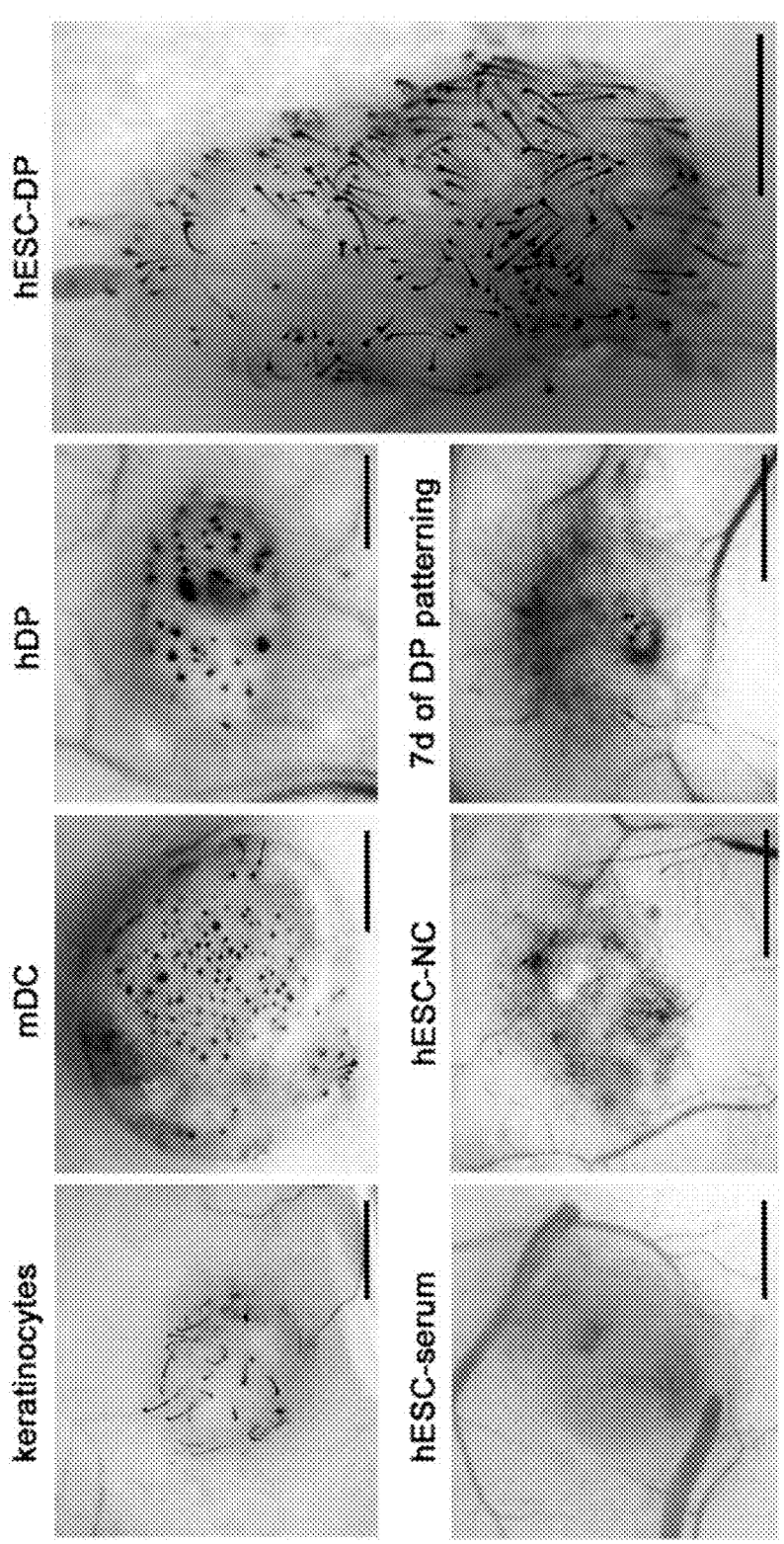
FIGS. 2A-2C depict effects of subcutaneous cell transplantations into Nude mice.
Figure 2B:
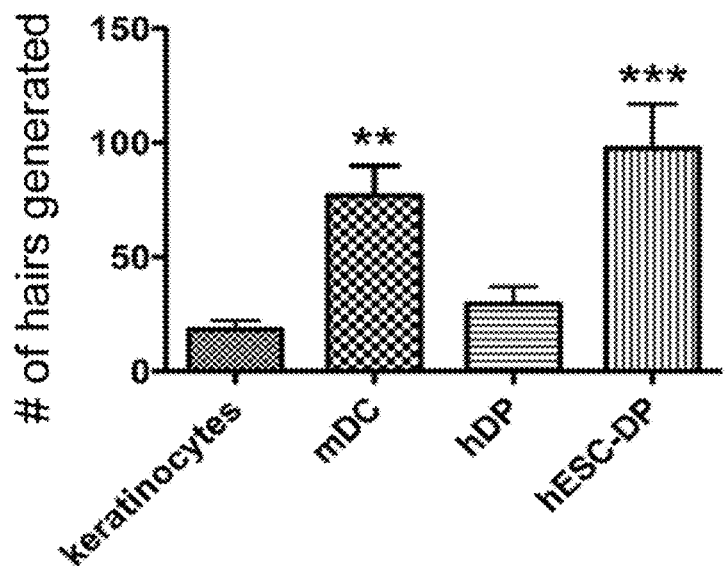

Whether hESC-DP cells are competent to induce the formation of hair follicles upon transplantation in athymic nu/nu (Nude) mice was investigated. The patch method of cell transplantation previously used to demonstrate the hair-inducing potential of mouse skin-derived dermal precursors was used [27]. Briefly, cells of interest were combined with mouse epidermal cells (keratinocytes) isolated from the newborn animals and transplanted subcutaneously into the Nude mice as a thick cell suspension. Because Nude mice have the BALB/c (albino) genetic background, newly formed and preexisting hairs were distinguishable by using the epidermal cells from dark haired C57BL/6 mice for transplantation. Hair-inducing capacity was measured as the number of hairs formed per transplant. Patch method does not allow newly formed hairs to enter the skin surface that perturbs hair follicle morphology on the advanced stages of morphogenesis. Therefore the analysis was carried out at 14 days post transplantation when hair follicles were formed, but not fully developed. Transplantation of epidermal cells alone resulted in minimal hair induction, likely due to the presence of endogenous DP cells (FIGS. 2A, 2B). The mouse dermal cells (mDC), used as the positive control, induced robust hair growth (P=0.0282) with efficiency similar to that reported previously for same transplantation model [27] (FIGS. 2A, 2B). As expected, cultured human DP cells isolated from adult scalp skin didn't induce a significant number of hairs compared to the negative control (keratinocytes alone) (FIGS. 2A, 2B). Indeed, human DP cells have been shown to contribute in trans-species reformation of single hairs [14] but the robust hair-inducing capability of human DP cells in the mouse model has not been reported [18]. In contrast, significant (P=0.0002) hair-induction by hESC-DPs similar to that of mDC was observed (FIGS. 2A, 2B).

Figure 2C:
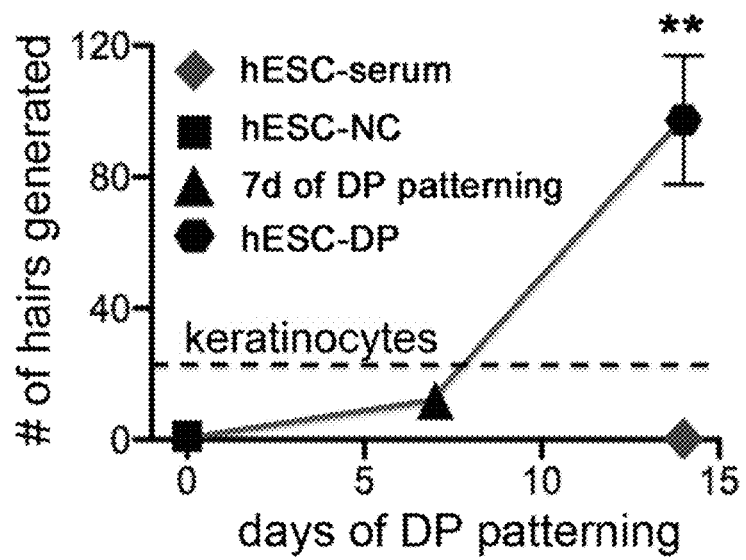

To monitor the dynamics of hair inducing properties during the differentiation of hESCs towards DP-like cells hESC-DPs and several related cell populations were transplanted, namely, hESC differentiated for two weeks in DP medium skipping the intermediate step of NC induction (hESC), hESC-NC and partially differentiated hESC-DPs (7 days of differentiation) (FIG. 2C). Surprisingly, the transplantation of the hESC differentiated in serum conditions as well as hESC-NC resulted in significant inhibition of hair growth compared to negative control (FIG. 2C). Therefore, the differentiation of hESC-NC to hESC-DPs cells resulted in nearly 100-fold increase in hair-inducing ability (FIG. 2C). The number of hairs formed in partially differentiated hESC-NCs transplants was not significantly different than in the negative control (FIG. 2C).

These results suggest that hESC-DP cells described here have a robust hair-inducing capacity similar to that of neonatal mouse dermal cells and that hESC-NCs acquire this capacity along the differentiation procedure.

hESC-DP Incorporate into DP of De Novo Formed Hair Follicles

Figure 3A:
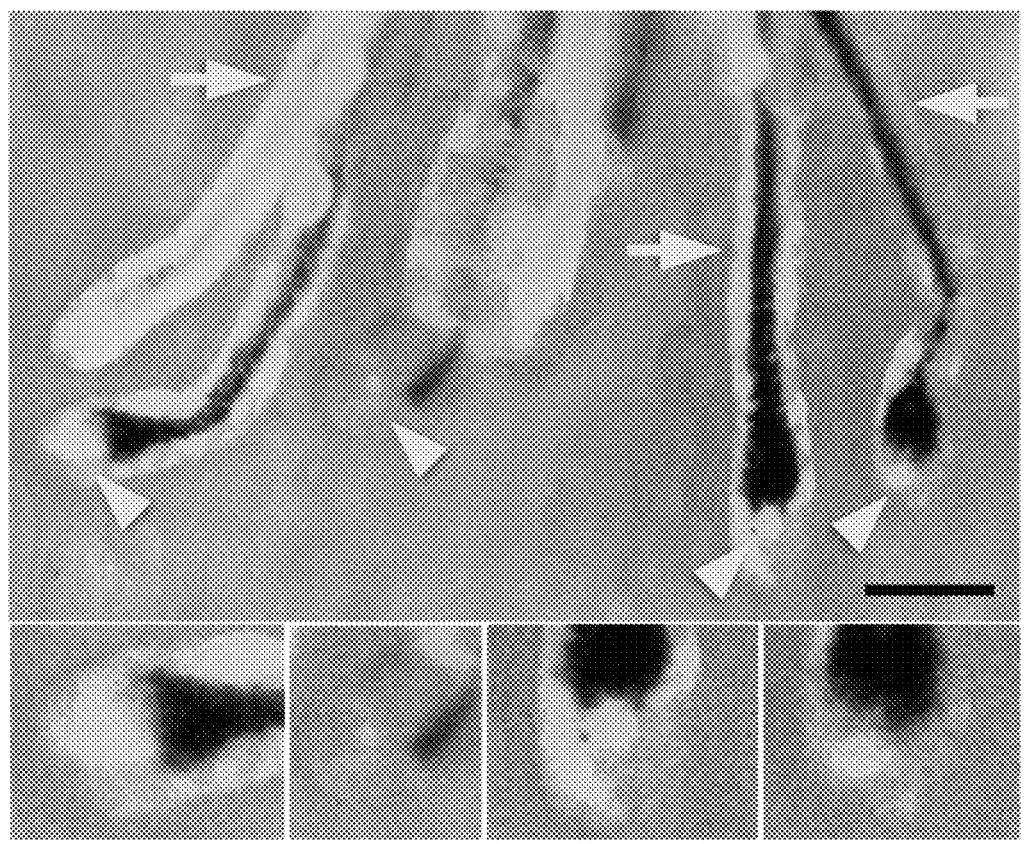
FIGS. 3A-3F depict subcutaneous transplantations of GFP-labeled hESC-DPs and hIPSC-DPs in a series of photomicrographs.
Figure 3B:
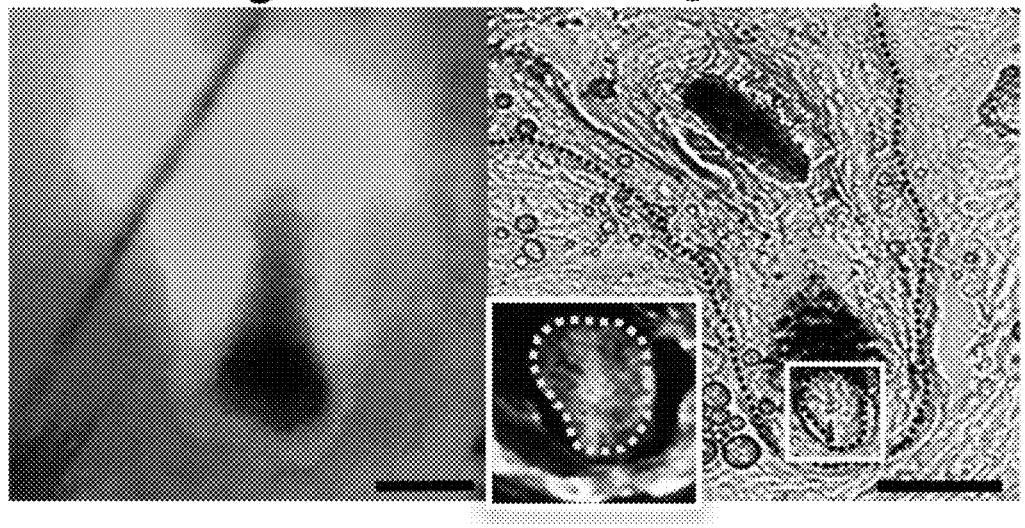
Figure 3C:
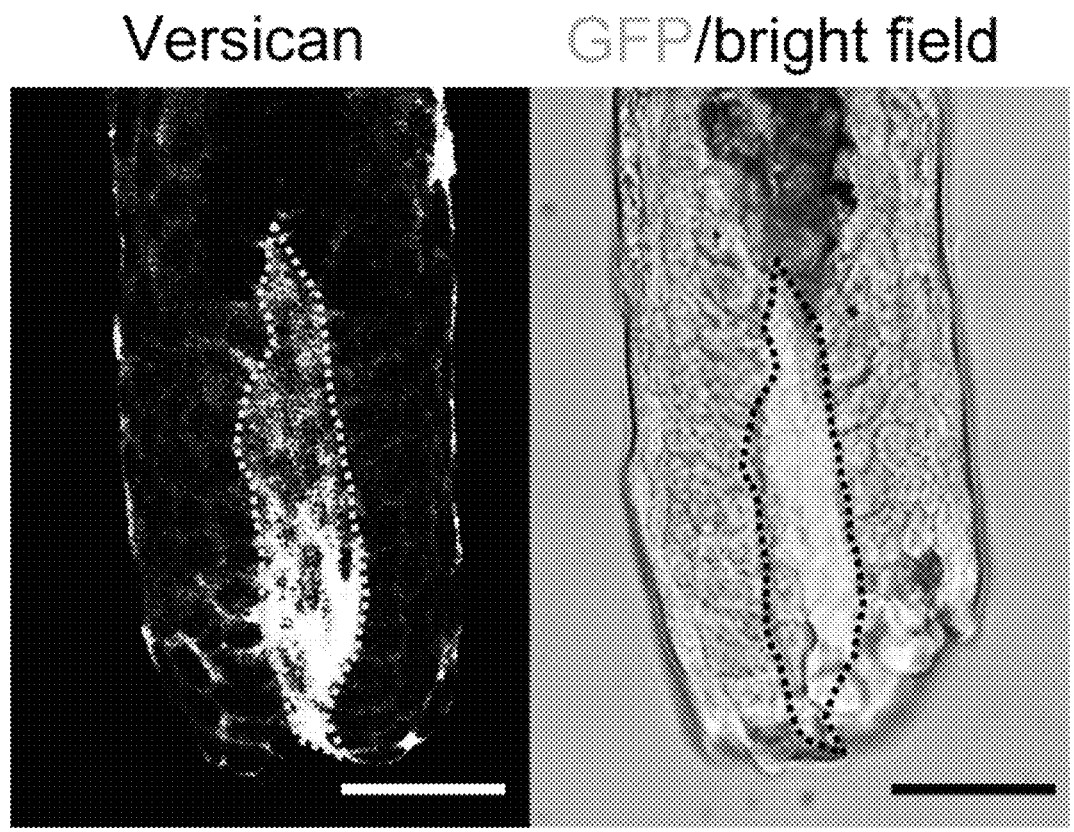
Figure 3D:
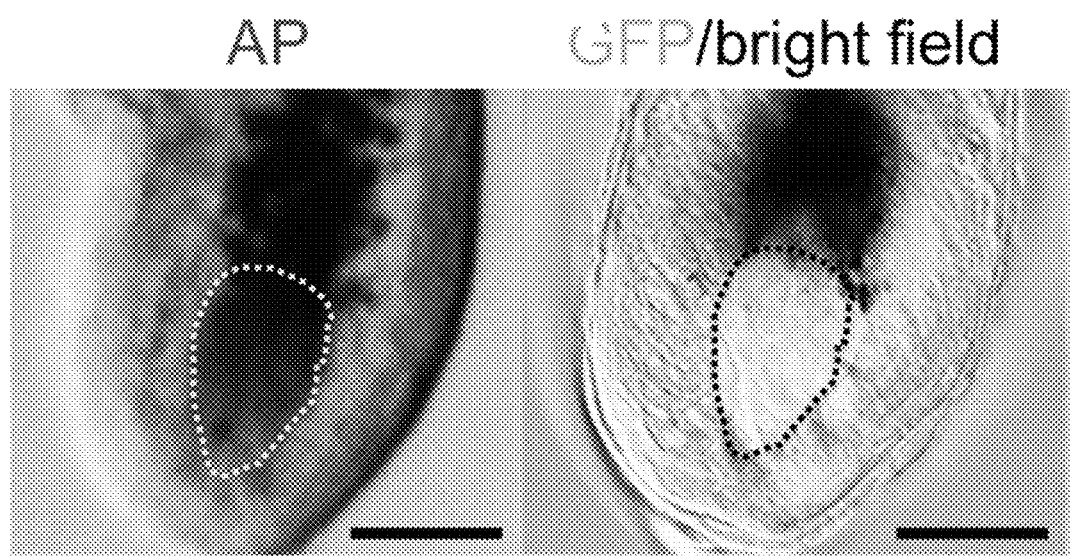
Figure 3E:
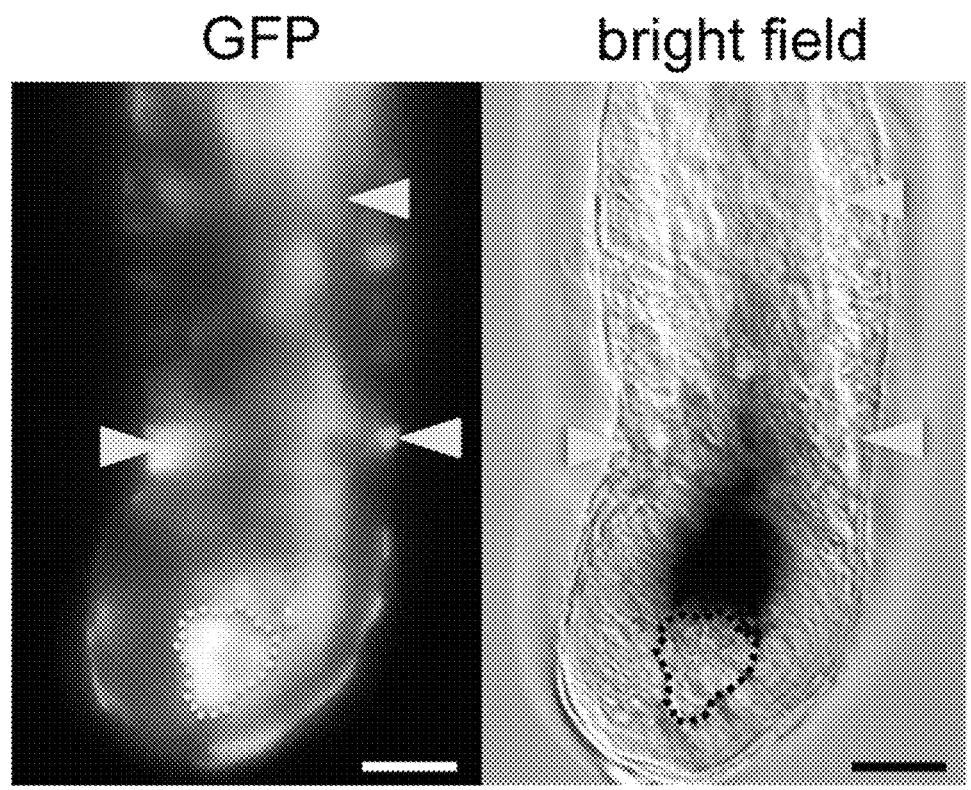
Figure 3F:
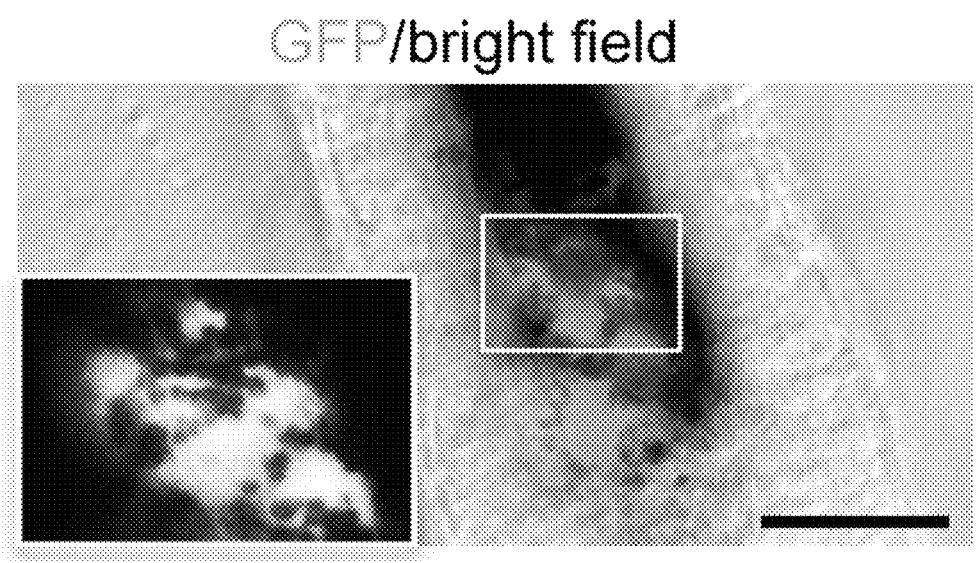

Transplanted hESC-DP may either recruit/activate endogenous mouse DP cells, or directly mediate the observed induction of hair follicle formation. To address this question hESC-DPs were engineered to express GFP and analyzed newly formed hair follicles in situ (FIG. 3). Fourteen days after transplantation under the skin of nude mice using the patch method a de novo hair formation that can be determined by the black pigmentation of the hair shafts was observed. Stereoscopic observation of hESC-DP transplants, suggested that the majority of DPs and dermal capsules of the newly formed hairs were composed of GFP-positive cells (FIG. 3A). Confocal microscopy of the whole mount hairs isolated from hESC-DP transplants showed the presence of GFP-positive DP cells within newly induced hairs (FIGS. 3C, 3D, 3E). GFP-positive DPs of these hairs stained positive for specific markers, namely, Versican (FIG. 3C) and AP (FIG. 3D). In addition to GFP-positive DPs, the presence of GFP-positive cells in the outer and the inner root sheaths area was observed (FIG. 3E). The presence of melanin granules in the cytoplasm of GFP-positive cells in the hair matrix was also observed (FIG. 3F). These data suggest that transplanted hESC-DP can acquire the hair-inducing function of DP cells.

Derivation and Characterization of hIPSC-DP

Figure 8A:
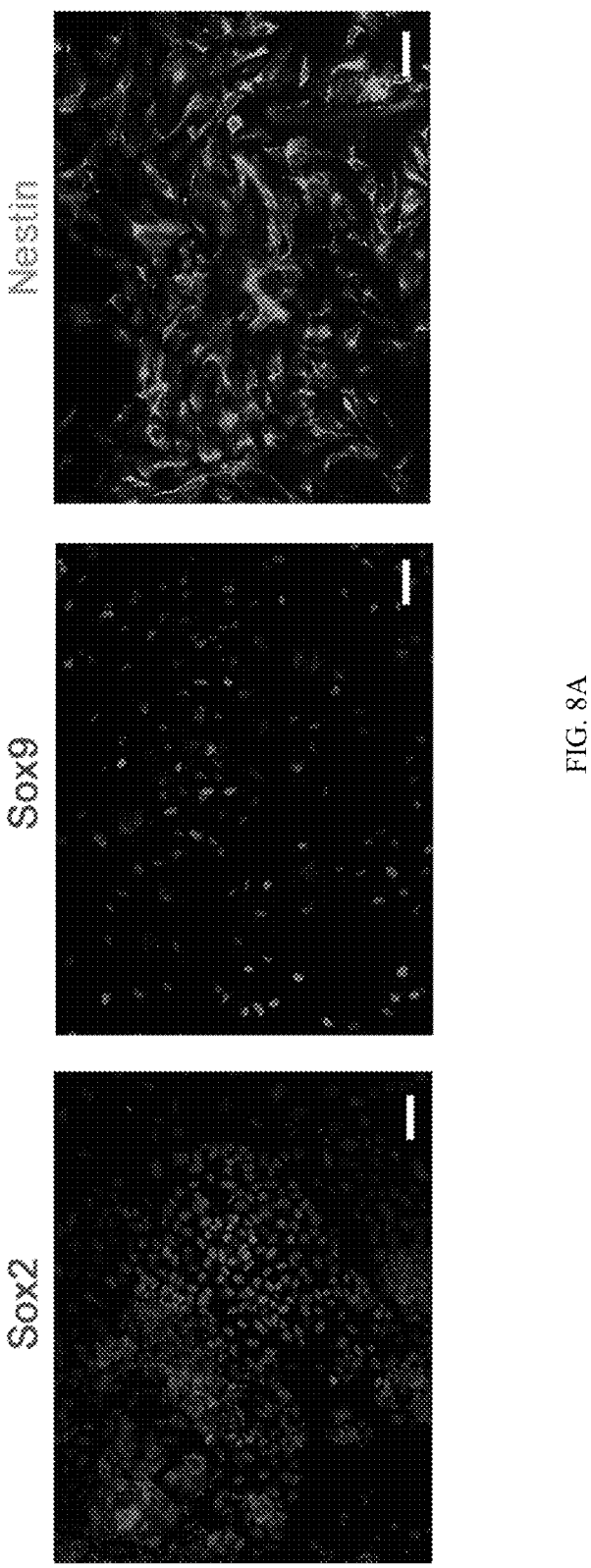
FIGS. 8A-8C depict differentiation of hIPSCs into DP-like cells via NC intermediate.
Figure 8B:
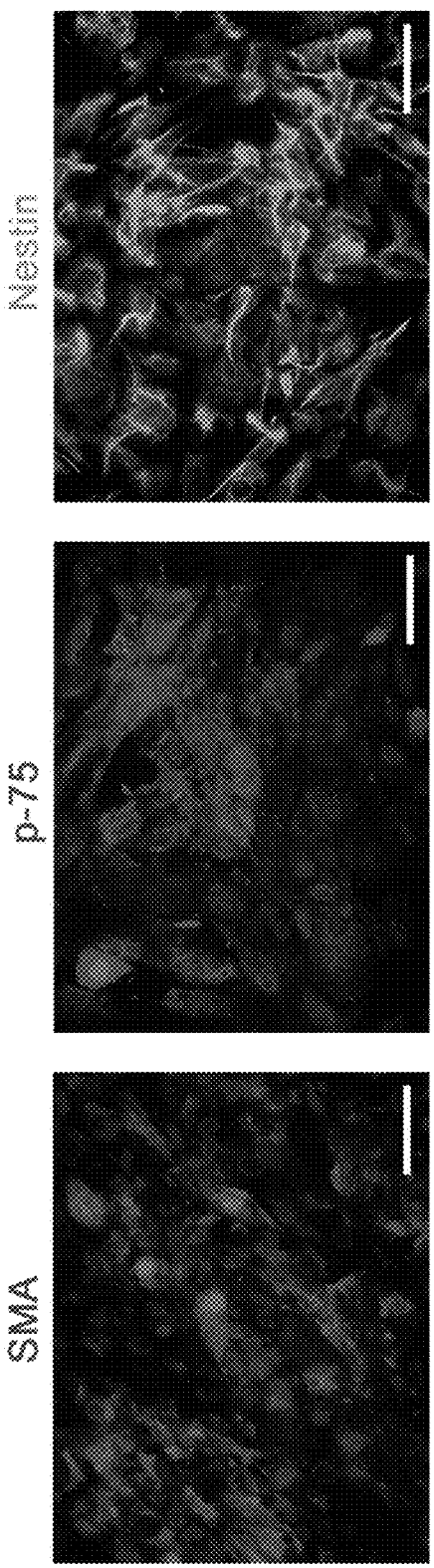
Figure 8C:
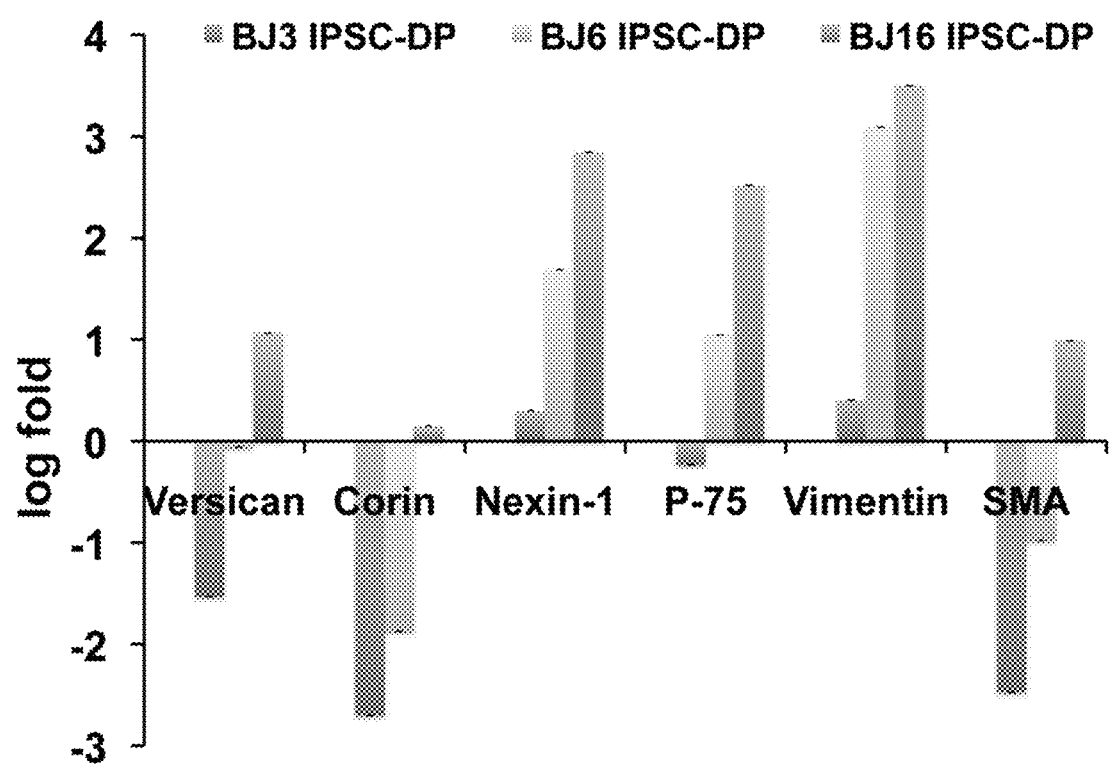

In addition to H9 line of human ESC, three previously characterized human induced pluripotent stem cells (hIPSC) lines generated from normal human BJ fibroblasts were used [30]. The hIPSC-NC cells were generated following previously described protocol and analyzed for the presence of neuroepithelial markers Sox2, Sox9 and nestin. hIPSC-NC obtained from all three lines showed a similar pattern of expression. Only about 50% of hIPSC-NC cells expressed Sox2 and Sox9, additionally nestin staining revealed morphological differences when compared to hESC-NC cells (FIG. 8A, FIG. 1D).

hIPSC-NC cells were differentiated to obtain hIPSC-DP using the protocol described above. The immunostaining for DP markers SMA, p-75 and nestin as well as Q-PCR analysis of Versican, Nexin-1, p-75, Vimentin and SMA showed that only one hIPSC line (BJ16) gave rise to cells with some expression of DP markers when compared to hESC-DP cells (FIG. 8B). FIG. 8C shows the levels of gene expression in hIPSC-DP relative to hESC-NC cells.

BJ16 IPSC-DP cells were further characterized by patch transplantation. This cell population did not induce significant number of hairs when compared to negative control. However, the transplantation of GFP-positive BJ16 IPSC-DP cells resulted in formation of hairs with GFP-positive dermal papillae and dermal capsules albeit with much lower frequencies (1 hair out of 50) then in case of hESC-DP cells. The presence of GFP-positive cells within DP of these hairs was confirmed in sections (FIG. 3B).

Figure 7:
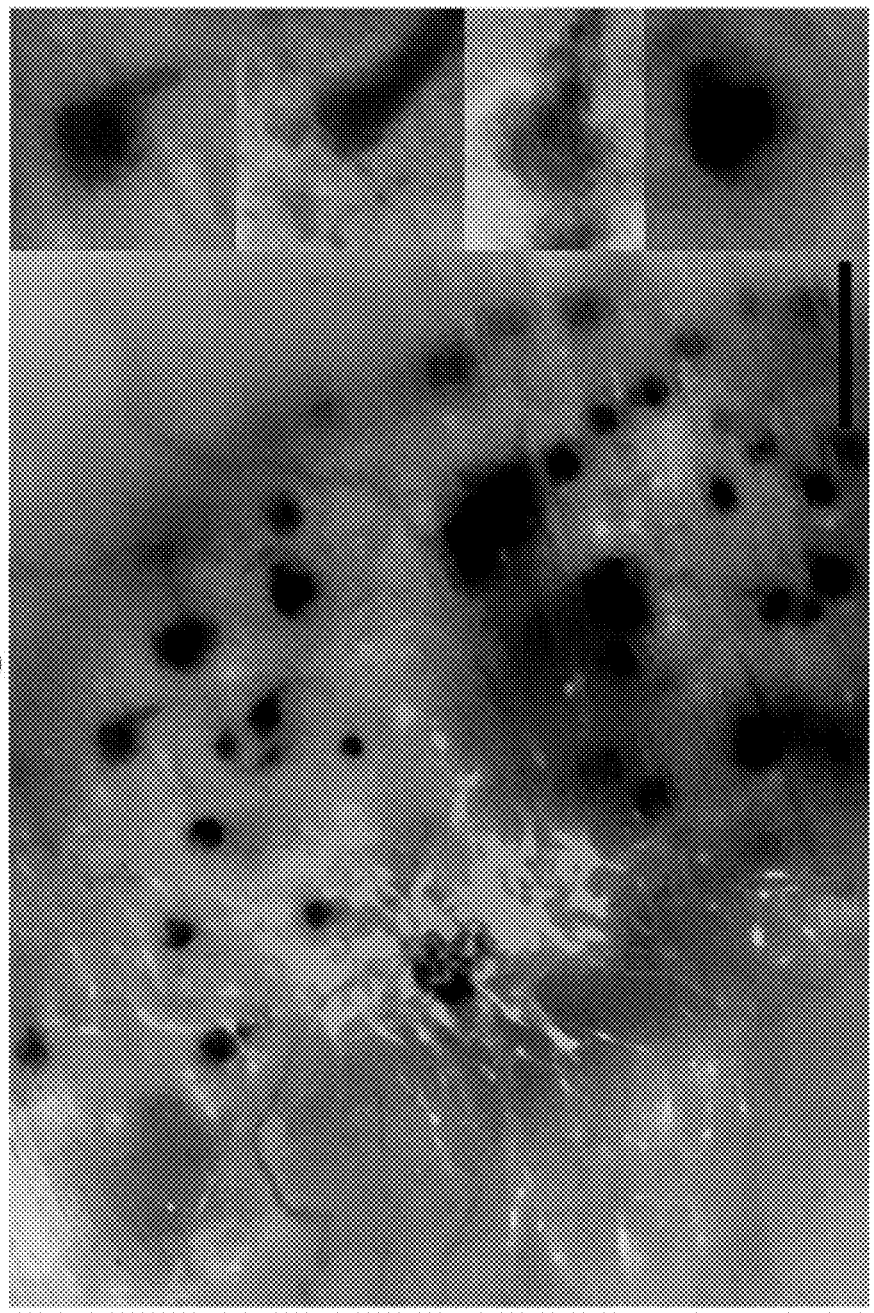
FIG. 7 is a series of photomicrographs depicting transplantation of human DP cells under the skin of Nude mice in which GFP-positive hDP cells can be found in dermis but do not incorporate into the DP areas of the newly formed hairs; whole mount transplant (insets shows 2× enlargements of the DP areas). Scale bar 250 μm.

Noteworthy, the integration of transplanted cells into the papillae and capsule area of newly formed hairs was observed only in the case of hESC-DP and hIPSC-DP cells. Although transplanted human DP cells engineered to express GFP were present in the dermis, these cells were not found in the DP of neighboring hair follicles (FIG. 7). These results suggest that although human pluripotent cell-derived DP-like cells share the expression of some specific markers with DP cells isolated from adult human skin, their hair-inducing capacity is higher and can be applied to the cell-based treatment of hair loss diseases.

Role of BMP Signaling in Derivation of hESC-DP

Figure 4A:
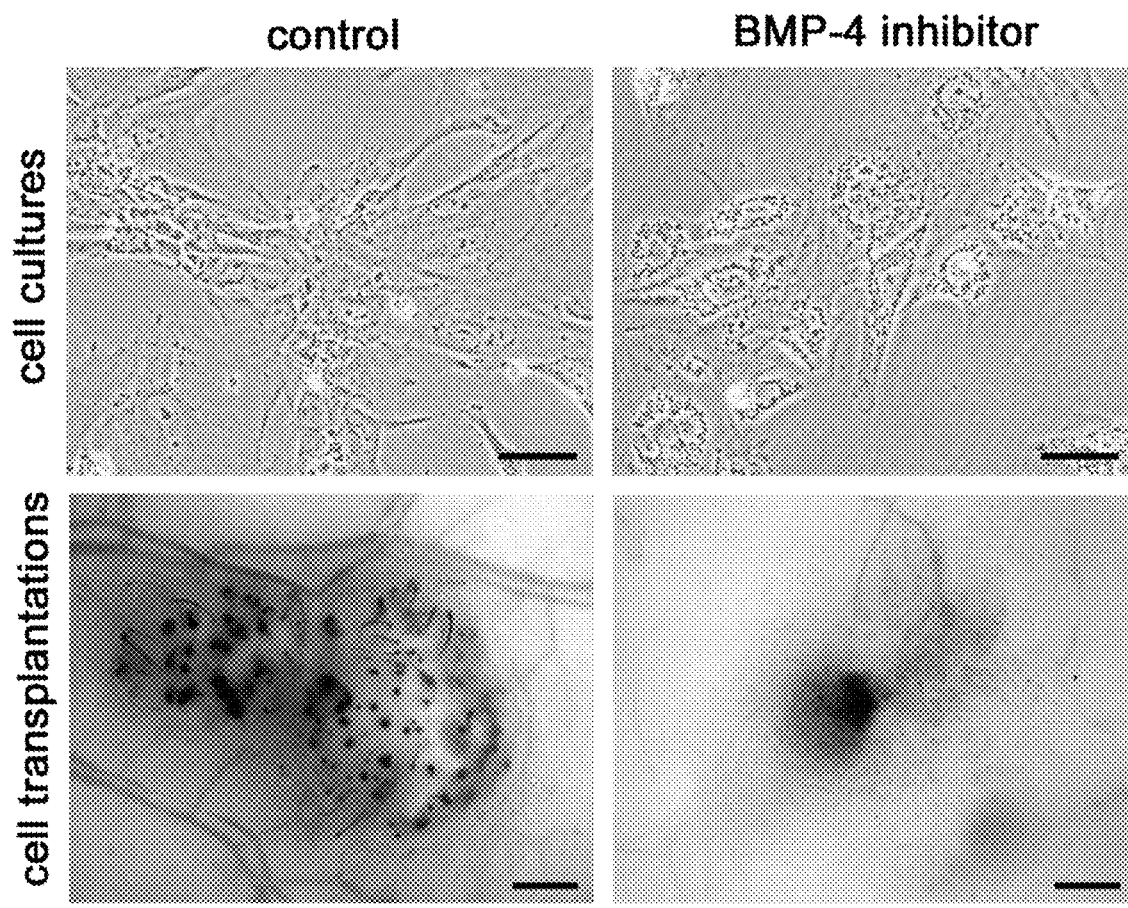
FIGS. 4A-4B depict a role of BMP signaling in DP cell fate acquisition.
Figure 4B:
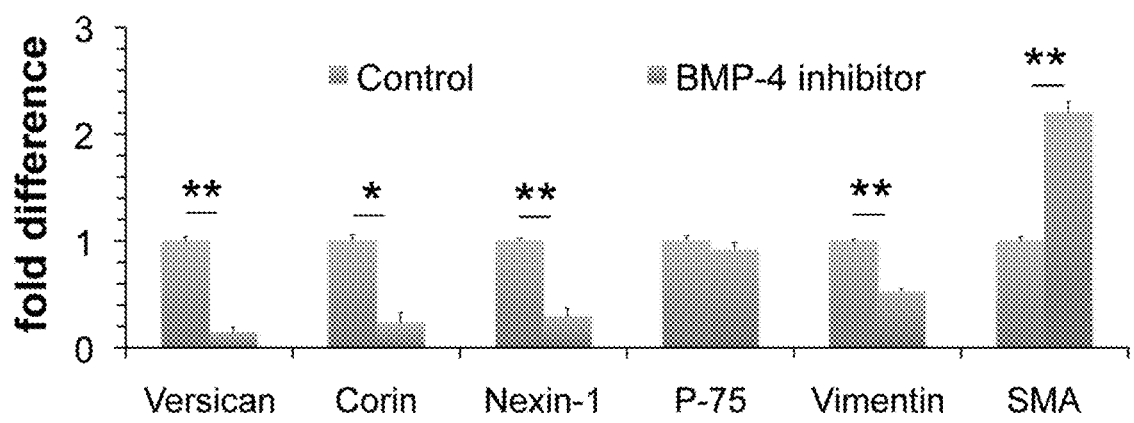

The mechanisms involved in generation of DP from migratory NC during development are unknown. However, fetal bovine serum used to induce DP differentiation from NC cells is known to contain bone morphogenetic proteins (BMPs) [31], which are essential in mesoderm specification during embryo development [32,33] and mesoderm induction from hESC in vitro [34]. BMP signaling was found to be a mechanism maintaining the hair follicle-inducing potential in mouse back skin DP [9]. Whether BMP signaling plays a role in the derivation of hESC-DP cells from hESC-NC cells using a well-studied selective BMP inhibitor dorsomorphin was investigated [35]. The addition of dorsomorphin during the NC to DP conversion resulted in obvious changes in cell morphology compared to the positive control, in particular, hESC-DP cells had characteristic fibroblast-like elongated morphology whereas dorsomorphin treated cells were hexagonal and demonstrated presence on multiple granules in their cytoplasm (FIG. 4A). Furthermore, dorsomorphin treated cells transplanted under the Nude mice skin were unable to induce hair formation suggesting the loss of DP properties (FIG. 4A). Q-PCR analysis of dorsomorphin treated cells revealed that the inhibition of BMP signaling resulted in significant decrease in levels of mRNAs encoding the DP-specific markers Versican ($P=0.0002$), Corin ($P=0.0022$), Nexin-1 ($P=0.0008$) and Vimentin ($P=0.0001$) but not the pan NC marker p-75 (not changed) or the smooth muscle marker SMA (significantly increased) (FIG. 4B). However, DP cells were not derivable from hESC-NC cultures using BMPs as the only differentiation agents suggesting other signaling pathways to be involved in cephalic DP cell fate acquisition. These results indicate that BMP signaling is necessary but not sufficient for the generation and/or maintenance of hair-inducing hESC-DP from hESC-NC cells.

The results suggest that hESC-derived NC cells cultured in serum-containing medium progressively acquire the markers of human DP cells and give rise to adherent cell population with hair-inducing potential. Robust hair-inducing capacity of hESC-DP as compared to human DP cells might reflect a major resemblance of the former to an embryonic or neonatal population of dermal papilla precursor cells, which are known to induce hair follicle formation through different mechanisms [36].

The hESC-DP cultures are likely to be heterogeneous. The average hair inducing capacity shown by these cultures was similar to that of neonatal mouse dermal cells. Prospectively purified primary mouse DP cells were shown to be about five times more efficient in hair induction than mouse dermal preparations [27]. Therefore, it is possible that hESC-DP cultures comprise a sub-population of hair inducing DP-like cells, with even higher heir-inducing capacity than the average reported above. Additionally, when GFP-positive hESC-DP were transplanted, the presence of GFP-positive cells in other compartments of hair follicles (i.e. outer root sheath, inner root sheath and hair matrix) was observed. Since melanocytes are known to originate from migratory NC during development, it is likely that some hESC-NC cells give rise to melanocyte precursors within hESC-DP cultures. Similarly, it is possible that some hESC-NCs are able to give rise to keratinocytes of newly formed hairs since rodent NC cells can give rise to the epidermal stem cells in the whisker's bulge [37]. These data suggest that hESC-DP is a mixed population of NC-derived cells that contain DP-like cells with hair-inducing properties, but also might contain melanocyte and keratinocyte forming cells.

The results suggest that the intermediate step of hESC differentiation into the NC lineage seems is critical, skipping the NC induction results in a complete loss of hair-inducing activity. Directing hESCs to the NC cells might limit the variety of mesenchymal cell types to the subset that is developmentally specified downstream from NC cells in skin (e.g. cephalic DP during development, melanocytes, cephalic bulge). Therefore, the hESC-DP-like cells become prominently enriched in heir-inducing DP-like cells using relatively common mesenchymal-enriching conditions such as differentiation in serum containing medium and selection for the adherent cell types.

Different iPSC lines may have variable propensity to differentiate towards DP-like cells. The hiPSC-DP cells were not able to induce hair follicle formation when transplanted using patch method and had low frequency of incorporation into the DP of newly formed hair follicles. This might be a result of the epigenetic memory phenomenon, known to influence IPSC differentiation [38,39,40]. The IPSC lines used for these experiments were derived from BJ fibroblasts [30]. Their mesodermal origin could cause difficulties on the first step of differentiation—induction of the ectodermal neural crest cells. Indeed, only some hIPSC-NC cells expressed neuroepithelial markers Sox2 and Sox9 (FIGS. 8A, 8B). However, a global comparison of multiple hiPCS and hESC lines suggested that when sufficiently large numbers of hiPSC lines were compared with hESC lines a major overlap in their differentiation potential was observed [41]. Therefore although the absolute efficiency may vary between different hESC and hiPSC lines it should be possible to derive cells with hair-inducing properties from many hiPSC [42].

Recently, SKPs were shown to be highly potent in hair induction [27], but progressive loss of SKPs in a process of aging might hamper the isolation of autologous SKPs for hair regenerative therapies for aged people [43]. The derivation of hair-inducing DP-like cells from hESCs represents the first step towards development of a cell-based treatment for people with hair loss.

Materials and Methods hESCs culture: H9 hESC line was maintained on eradiated mouse embryonic fibroblast feeder layers as previously described [24]. Generation of NC cells from hESC: the differentiation protocol is previously described [24,25]. Generation of ESC-DP: NC cells on passage one were cultured for 3 days with DP Medium of the following composition: DMEM/F-12 Glutamax (Gibco 10829-018), 10% FBS (Gibco #10437), 1 mM L-glutamine (Gibco 25030-081), 1× antibiotic/antimycotic (Omega Scientific AA-40). After that, they were dissociated to single-cell suspension with 0.25% Trypsin-EDTA solution (Gibco 25200) and plated on uncoated culture dishes in density 100 thousands cells/mm$^{-2}$. Floating cells failed to attach after 24 hours were removed with medium change on the following day. Attached cells were grown on uncoated plastic dishes with Medium change every other day; culture was passed every 4-5 days.

Immunohistochemistry and FACS analysis: cell cultures were fixed with 4% PFA in PBS for 10 minutes at room temperature; tissue samples were fixed at 4° overnight. After fixation cells were washed in PBS 3 times for 5 minutes, and tissue samples were embedded in OCT for frozen sections or used for hair dissections and whole mount preparations. Cells and sections were blocked in 4% BSA or 10% goat serum with 0.05%-0.3% Triton×100 (Sigma T8787) in PBS for one hour prior to staining. Primary antibodies were applied over night at 4° C. Cells or sections were then washed in PBS for 3 times 15 minutes each. Secondary antibodies (diluted 1:500 in PBS) were applied for 1 hour at room temperature in dark. Cells were washed in PBS for 3 times 10 minutes each. Nuclei were labeled with Hoechst or Dapi. For FACS analysis, cells of interest were detached with Accutase and resuspended in 3% BSA/PBS for 20 minutes to block non-specific binding. Then cells were incubated with primary antibodies for 30 minutes on ice. Then cells were washed in 3 ml of PBS and resuspended in 3% BSA/PBS with appropriate secondary antibodies (1:1000) for 30 minutes and washed with 3 ml of PBS before being resuspended in 1% BSA/PBS and incubated with propidium iodide (PI). Cells were sorted according to fluorescence (FACSVantageSE DiVa, BD Biosciences, San Jose) and data were analyzed with FlowJo software. The following antibodies were used: mouse monoclonal CD47 (R&D), mouse monoclonal CD184 (eBioscience), mouse monoclonal CD44 (Novus), goat polyclonal Foxd3 (Santa Cruz), rabbit polyclonal GFP (Invitrogen), mouse monoclonal ITGA4 (R&D), mouse monoclonal Nestin (Chemicon), mouse monoclonal OCT3/4 (Santa Cruz), rabbit polyclonal P-75 (Chemicon), mouse monoclonal SMA (Chemicon), rabbit polyclonal Sox2 (Abcam), rabbit polyclonal Sox9 (Millipore), rabbit polyclonal Sox10 (Abcam), mouse monoclonal SSEA4 (R&D), mouse monoclonal Versican (Seikagaku Corporation).

Q-PCR: total RNA was extracted using the RNeasy kit and 1 μg of total RNA was reverse transcribed using the Quantitect kit (Qiagen) according to the manufacturer's suggestions to make cDNA. Q-PCR was performed with SyberGreen master mix (Invitrogen) according to the manufacturer's recommendation. For Q-PCR, 18S expression level was used for normalization and the data were analyzed using the standard curve method. Q-PCR was performed as follows: initial denaturation: 10 min at 95° C.; 40 cycles of denaturation: 30 sec at 95° C., annealing: 1 min at 56° C., extension: 30 sec at 72° C.; and one final cycle of denaturation for 1 min at 95° C., annealing for 30 sec at 65° C. and final denaturation for 30 sec at 95° C. Real time Q-PCR primers are summarized in TABLE 1.

TABLE 1

| Primer | Sequence | SEQ ID NO: |
| --- | --- | --- |
| 18S forward | AGTCCCTGCCCTTTGTACACA | SEQ ID NO: 01 |
| 18S reverse | CGATCCGAGGGCCTCACTA | SEQ ID NO: 02 |
| Corin forward | AACCCAGTGGACATATCTGTGGCT | SEQ ID NO: 03 |
| Corin reverse | TGTTGATGCCAAGCACCACTTTCC | SEQ ID NO: 04 |
| Nexin forward | TGTGAAGTCGAGGCCTCATGACAA | SEQ ID NO: 05 |
| Nexin reverse | TCTTGGAGACGATGGCCTTGTTGA | SEQ ID NO: 06 |
| P-75 forward | TTCAAGGGCTTACACGTGGAGGAA | SEQ ID NO: 07 |
| P-75 reverse | AATTCCTTCTTGCCGCATTCCCAC | SEQ ID NO: 08 |
| Versican forward | TGAGCATGACTTCCGTTGGACTGA | SEQ ID NO: 09 |
| Versican reverse | CCACTGGCCATTCTCATGCCAAAT | SEQ ID NO: 10 |
| Vimentin forward | AGAACCTGCAGGAGGCAGAAGAAT | SEQ ID NO: 11 |
| Vimentin reverse | TTCCATTTCACGCATCTGGCGTTC | SEQ ID NO: 12 |

Cells: ESC-DP cells on different passages were obtained. Cells were dissociated to single-cell suspension with 0.1% Trypsin-EDTA (Gibco 25200) and washed 3 times with PBS by serial centrifuging (1200 RPM for 5 minutes). Finally cells were resuspended in DP medium at concentration 5 million per 100 μl and kept on ice until transplanted.

Mouse epidermal and dermal cells were obtained from p0-p2 BL6 mice skin. Back skins were isolated and placed on ice, washed in PBS with antibiotic/antimycotic (final 1×; Omega Scientific AA-40) 5 times for 5 minutes shaking and incubated in 0.01% Dispase (Sigma) in PBS overnight at 40° C. Epidermal layers of skins were isolated with forceps, washed in PBS for 5 min and incubated in 0.1% Trypsin-EDTA solution at 370 C for 8 minutes. Dermal layers of skin were homogenized with scissors and digested with 0.1% Trypsin-EDTA solution at 370 C for 45 minutes. Enzyme activity was blocked with addition of DP medium and epidermises or dermises were pipetted vigorously for 10 minutes. Cell suspension was isolated with cell strainer (BD Falcon 9261365) and washed in PBS by centrifuging 3 times (1200 RPM for 5 minutes). Cells were resuspended in DP medium at 5 million cells per 100 μl and kept on ice until transplanted.

Human dermal papillae cells: the use of human tissue-derived samples in this study was limited to use of skin waste tissue from 2 cosmetic medical procedures. Skins were washed in PBS with antibiotic/antimycotic (final 1×; Omega Scientific AA-40) 15 times for 5 minutes shaking. Then fat containing hair follicles was isolated with scalpel and incubated in 0.2% Dispase (Sigma) in DMEM/F12 overnight at 40° C. Hair follicles were isolated from fat with the forceps and incubated in 0.1% Collagenase type I (Sigma) in DMEM/F12 for 5-7 hours. Then DPs were detached from the rest of follicles by vigorous pipetting for 10 minutes. After hair follicles settle on the bottom DP staid in supernatant and were isolated by centrifuging 1000 RPM for 5 minutes.

Cell transplantation: the method of cell transplantation was described previously in detail [27]. Briefly, 100 μl of suspension ($5 \times 10^5$ cells) of cells of interest (ESC-NC, early ESC-DP, ESC-DP, rDP p2) were combined with 100 μl of suspension of epidermal cells ($5 \times 10^5$ cells) and transplanted with subcutaneous injections to immunodeficient mice (strain Athymic Nu/Nu). After 14-21 days mice were euthanized and transplants were analyzed. For negative control epidermal cells alone were transplanted.

REFERENCES

Each of the following references is expressly incorporated herein by reference in its entirety.
1. Hardy M H (1992) The secret life of the hair follicle. Trends Genet 8: 55-61.
2. Jahoda C A, Reynolds A J (1996) Dermal-epidermal interactions. Adult follicle-derived cell populations and hair growth. Dermatol Clin 14: 573-583.
3. Millar S E (2002) Molecular mechanisms regulating hair follicle development. J Invest Dermatol 118: 216-225.
4. Driskell R R, Clavel C, Rendl M, Watt F M (2011) Hair follicle dermal papilla cells at a glance. J Cell Sci 124: 1179-1182.
5. Schmidt-Ullrich R, Paus R (2005) Molecular principles of hair follicle induction and morphogenesis. Bioessays 27: 247-261.
6. Botchkarev V A, Paus R (2003) Molecular biology of hair morphogenesis: development and cycling. J Exp Zool B Mol Dev Evol 298: 164-180.
7. Rendl M, Lewis L, Fuchs E (2005) Molecular dissection of mesenchymal-epithelial interactions in the hair follicle. PLoS Biol 3: e331.
8. Kishimoto J, Burgeson R E, Morgan B A (2000) Wnt signaling maintains the hair-inducing activity of the dermal papilla. Genes Dev 14: 1181-1185.
9. Rendl M, Polak L, Fuchs E (2008) BMP signaling in dermal papilla cells is required for their hair follicle-inductive properties. Genes Dev 22: 543-557.
10. Greco V, Chen T, Rendl M, Schober M, Pasolli H A, et al. (2009) A two-step mechanism for stem cell activation during hair regeneration. Cell Stem Cell 4: 155-169.
11. Weinberg W C, et al. (1993) Reconstitution of hair follicle development in vivo: determination of follicle formation, hair growth, and hair quality by dermal cells. J Invest Dermatol 100: 229-236.
12. Driskell R R, Giangreco A, Jensen K B, Mulder K W, Watt F M (2009) Sox2-positive dermal papilla cells specify hair follicle type in mammalian epidermis. Development 136: 2815-2823.
13. Jahoda C A, Home K A, Oliver R F (1984) Induction of hair growth by implantation of cultured dermal papilla cells. Nature 311: 560-562.
14. Jahoda C A, et al. (2001) Trans-species hair growth induction by human hair follicle dermal papillae. Exp Dermatol 10: 229-237.
15. Wu J J, et al. (2006) Hair follicle reformation induced by dermal papilla cells from human scalp skin. Arch Dermatol Res 298: 183-190.
16. Chermnykh E S, et al. (2010) Dermal papilla cells induce keratinocyte tubulogenesis in culture. Histochem Cell Biol 133: 567-576.
17. Lichti U, et al. (1993) In vivo regulation of murine hair growth: insights from grafting defined cell populations onto nude mice. J Invest Dermatol 101: 124S-1295.
18. Yang C C, Cotsarelis G (2010) Review of hair follicle dermal cells. J Dermatol Sci 57: 2-11.
19. Bronner-Fraser M (1994) Neural crest cell formation and migration in the developing embryo. FASEB J 8: 699-706.
20. Danielian P S, Muccino D, Rowitch D H, Michael S K, McMahon A P (1998) Modification of gene activity in mouse embryos in utero by a tamoxifen-inducible form of Cre recombinase. Curr Biol 8: 1323-1326.
21. Fernandes K J, et al. (2004) A dermal niche for multipotent adult skin-derived precursor cells. Nat Cell Biol 6: 1082-1093.
22. Nagoshi N, et al. (2008) Ontogeny and multipotency of neural crest-derived stem cells in mouse bone marrow, dorsal root ganglia, and whisker pad. Cell Stem Cell 2: 392-403.
23. Metallo C M, Ji L, de Pablo J J, Palecek S P (2008) Retinoic acid and bone morphogenetic protein signaling synergize to efficiently direct epithelial differentiation of human embryonic stem cells. Stem Cells 26: 372-380.
24. Curchoe C L, et al. (2010) Early acquisition of neural crest competence during hESCs neuralization. PLoS One 5: e13890.
25. Cimadamore F, et al. (2011) Human ESC-Derived Neural Crest Model Reveals a Key Role for SOX2 in Sensory Neurogenesis. Cell Stem Cell 8: 538-551.
26. Mould A P, et al. (1994) Integrin alpha 4 beta 1-mediated melanoma cell adhesion and migration on vascular cell adhesion molecule-1 (VCAM-1) and the alternatively spliced IIICS region of fibronectin. J Biol Chem 269: 27224-27230.
27. Biernaskie J, Paris M, Morozova O, Fagan B M, Marra M, et al. (2009) SKPs derive from hair follicle precursors and exhibit properties of adult dermal stem cells. Cell Stem Cell 5: 610-623.
28. Hoogduijn M J, Gorjup E, Genever P G (2006) Comparative characterization of hair follicle dermal stem cells and bone marrow mesenchymal stem cells. Stem Cells Dev 15: 49-60.
29. Pittenger M F, et al. (1999) Multilineage potential of adult human mesenchymal stem cells. Science 284: 143-147.
30. Liu G H, et al. (2011) Recapitulation of premature ageing with iPSCs from Hutchinson-Gilford progeria syndrome. Nature.
31. Kodaira K, et al. (2006) Purification and identification of a BMP-like factor from bovine serum. Biochem Biophys Res Commun 345: 1224-1231.
32. Winnier G, Blessing M, Labosky P A, Hogan B L (1995) Bone morphogenetic protein-4 is required for mesoderm formation and patterning in the mouse. Genes Dev 9: 2105-2116.

33. Mishina Y, Suzuki A, Ueno N, Behringer R R (1995) Bmpr encodes a type I bone morphogenetic protein receptor that is essential for gastrulation during mouse embryogenesis. Genes Dev 9: 3027-3037.
34. Zhang P, Li J, Tan Z, Wang C, Liu T, et al. (2008) Short-term BMP-4 treatment initiates mesoderm induction in human embryonic stem cells. Blood 111: 1933-1941.
35. Yu P B, et al. (2008) Dorsomorphin inhibits BMP signals required for embryogenesis and iron metabolism. Nat Chem Biol 4: 33-41.
36. Inamatsu M, et al. (2006) Embryonic dermal condensation and adult dermal papilla induce hair follicles in adult glabrous epidermis through different mechanisms. Dev Growth Differ 48: 73-86.
37. Sieber-Blum M, Grim M (2004) The adult hair follicle: cradle for pluripotent neural crest stem cells. Birth Defects Res C Embryo Today 72: 162-172.
38. Kim K, et al. (2010) Epigenetic memory in induced pluripotent stem cells. Nature 467: 285-290.
39. Jandial R, Levy M L (2011) Cellular alchemy: induced pluripotent stem cells retain epigenetic memory. World Neurosurg 75: 5-6.
40. Bar-Nur O, Russ H A, Efrat S, Benvenisty N (2011) Epigenetic memory and preferential lineage-specific differentiation in induced pluripotent stem cells derived from human pancreatic islet Beta cells. Cell Stem Cell 9: 17-23.
41. Boulting G L, et al. (2011) A functionally characterized test set of human induced pluripotent stem cells. Nat Biotechnol 29: 279-286.
42. Bock C, et al. (2011) Reference Maps of human ES and iPS cell variation enable high-throughput characterization of pluripotent cell lines. Cell 144: 439-452.
43. Zouboulis C C, Adjaye J, Akamatsu H, Moe-Behrens G, Niemann C (2008) Human skin stem cells and the ageing process. Exp Gerontol 43: 986-997.

The term "comprising" as used herein is synonymous with "including," "containing," or "characterized by," and is inclusive or open-ended and does not exclude additional, unrecited elements or method steps.

The above description discloses several methods and materials of the present invention. This invention is susceptible to modifications in the methods and materials, as well as alterations in the fabrication methods and equipment. Such modifications will become apparent to those skilled in the art from a consideration of this disclosure or practice of the invention disclosed herein. Consequently, it is not intended that this invention be limited to the specific embodiments disclosed herein, but that it cover all modifications and alternatives coming within the true scope and spirit of the invention.

All references cited herein, including but not limited to published and unpublished applications, patents, and literature references, are incorporated herein by reference in their entirety and are hereby made a part of this specification. To the extent publications and patents or patent applications incorporated by reference contradict the disclosure contained in the specification, the specification is intended to supersede and/or take precedence over any such contradictory material.

What is claimed is:

1. A method for preparing a population of induced dermal papillae cells comprising:
   (a) obtaining a population of human induced pluripotent stem cells (hIPSCs);
   (b) differentiating the population of hIPSCs into a population of human induced pluripotent stem cell-derived neural crest cells (hIPSC-NC), wherein the population of hIPSC-NC lack a marker selected from the group consisting of versican, smooth muscle actin, and alkaline phosphatase; and
   (c) differentiating the population of hIPSC-NC into a population of human induced pluripotent stem cell-derived dermal papillae-like cells (hIPSC-DP), wherein differentiating the population of hIPSC-NC comprises selecting adherent cells from the population of hIPSC-NC.

2. The method of claim 1, wherein the population of human induced pluripotent stem cells are generated from a source selected from the group consisting of fibroblasts, renal epithelial cells, and blood cells.

3. The method of claim 1, wherein the population of human induced pluripotent stem cells are generated from human BJ fibroblasts.

4. The method of claim 1, wherein step (b) further comprises culturing the population of human induced pluripotent stem cells under conditions to form clusters.

5. The method of claim 4, wherein the clusters are in suspension to form spheres.

6. The method of claim 5, wherein the spheres are plated on the surface of a substrate, and wherein the surface is coated with fibronectin or polyornithine.

7. The method of claim 1, wherein step (b) further comprises analyzing the population of hIPSC-NC to confirm the presence of a marker selected from the group consisting of Sox10, Foxd3, integrin alpha 4, cognate receptor for fibronectin, CD47, CD 184, CD44, P-75, and nestin.

8. The method of claim 1, wherein step (b) further comprises analyzing the hIPSC-NC to confirm the absence of a marker selected from the group consisting of OCT4 and SSEA4.

9. The method of claim 1, wherein step (c) further comprises analyzing the hIPSC-DP to confirm the presence of a marker selected from the group consisting of P-75, nestin, versican, smooth muscle actin, alkaline phosphatase, and vimentin.

10. The method of claim 1, further comprising:
    (d) administering the hIPSC-DP to a subject in need thereof.

11. The method of claim 10, wherein the hIPSCs are obtained from the subject in need thereof.

12. The method of claim 10, wherein the hIPSCs are not obtained from the subject in need thereof.

13. The method of claim 10, wherein the administering comprises subcutaneous transplantation.

14. The method of claim 10, further comprising administering to a location comprising hair on a skin of the subject in need thereof.

15. The method of claim 14, wherein the location is selected from the group consisting of scalp, face, upper lip, chin, eyebrow, eyelash, arm, leg, back, torso, and abdomen.

16. The method of claim 14, wherein the location comprises scar tissue.

17. The method of claim 10, wherein the subject has alopecia.

* * * * *

UNITED STATES PATENT AND TRADEMARK OFFICE
CERTIFICATE OF CORRECTION

PATENT NO. : 10,716,808 B2
APPLICATION NO. : 15/320529
DATED : July 21, 2020
INVENTOR(S) : Terskikh Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 419 days.

Signed and Sealed this
Fourteenth Day of February, 2023

Katherine Kelly Vidal
*Director of the United States Patent and Trademark Office*

SEQUENCE LISTING

```
<160> NUMBER OF SEQ ID NOS: 12

<210> SEQ ID NO 1
<211> LENGTH: 21
<212> TYPE: DNA
<213> ORGANISM: Homo sapiens

<400> SEQUENCE: 1
agtccctgcc ctttgtacac a                                        21

<210> SEQ ID NO 2
<211> LENGTH: 19
<212> TYPE: DNA
<213> ORGANISM: Homo sapiens

<400> SEQUENCE: 2
cgatccgagg gcctcacta                                           19

<210> SEQ ID NO 3
<211> LENGTH: 24
<212> TYPE: DNA
<213> ORGANISM: Homo sapiens

<400> SEQUENCE: 3
aacccagtgg acatatctgt ggct                                     24

<210> SEQ ID NO 4
<211> LENGTH: 24
<212> TYPE: DNA
<213> ORGANISM: Homo sapiens

<400> SEQUENCE: 4
tgttgatgcc aagcaccact ttcc                                     24
```

<210> SEQ ID NO 5
<211> LENGTH: 24
<212> TYPE: DNA
<213> ORGANISM: Homo sapiens

<400> SEQUENCE: 5
tgtgaagtcg aggcctcatg acaa					24

<210> SEQ ID NO 6
<211> LENGTH: 24
<212> TYPE: DNA
<213> ORGANISM: Homo sapiens

<400> SEQUENCE: 6
tcttggagac gatggccttg ttga					24

<210> SEQ ID NO 7
<211> LENGTH: 24
<212> TYPE: DNA
<213> ORGANISM: Homo sapiens

<400> SEQUENCE: 7
ttcaagggct tacacgtgga ggaa					24

<210> SEQ ID NO 8
<211> LENGTH: 24
<212> TYPE: DNA
<213> ORGANISM: Homo sapiens

<400> SEQUENCE: 8
aattccttct tgccgcattc ccac					24

<210> SEQ ID NO 9
<211> LENGTH: 24
<212> TYPE: DNA
<213> ORGANISM: Homo sapiens

<400> SEQUENCE: 9
tgagcatgac ttccgttgga ctga					24

<210> SEQ ID NO 10
<211> LENGTH: 24
<212> TYPE: DNA
<213> ORGANISM: Homo sapiens

<400> SEQUENCE: 10
ccactggcca ttctcatgcc aaat					24

<210> SEQ ID NO 11
<211> LENGTH: 24
<212> TYPE: DNA
<213> ORGANISM: Homo sapiens

<400> SEQUENCE: 11
agaacctgca ggaggcagaa gaat					24

<210> SEQ ID NO 12
<211> LENGTH: 24

```
<212> TYPE: DNA
<213> ORGANISM: Homo sapiens

<400> SEQUENCE: 12
ttccatttca cgcatctggc gttc                                              24
```